(12) United States Patent
Wilson et al.

(10) Patent No.: US 9,778,390 B2
(45) Date of Patent: Oct. 3, 2017

(54) ELECTROMAGNETIC IMAGING FOR STRUCTURAL INSPECTION

(71) Applicant: Halliburton Energy Services, Inc., Houston, TX (US)

(72) Inventors: Glenn A. Wilson, Singapore (SG); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/772,183

(22) PCT Filed: Oct. 8, 2014

(86) PCT No.: PCT/US2014/059738
§ 371 (c)(1),
(2) Date: Sep. 2, 2015

(87) PCT Pub. No.: WO2016/057033
PCT Pub. Date: Apr. 14, 2016

(65) Prior Publication Data
US 2016/0282504 A1 Sep. 29, 2016

(51) Int. Cl.
*G01V 3/38* (2006.01)
*E21B 47/00* (2012.01)
(Continued)

(52) U.S. Cl.
CPC ............ *G01V 3/38* (2013.01); *E21B 47/0002* (2013.01); *E21B 47/0006* (2013.01);
(Continued)

(58) Field of Classification Search
CPC .......... G01V 3/12; G01V 3/082; G01V 1/008; G01V 3/28; G01V 3/30
(Continued)

(56) References Cited

U.S. PATENT DOCUMENTS 3,241,102 A * 3/1966 Peterson ................ G01V 1/245
346/33 C
3,535,920 A * 10/1970 Bernaix ................... G01B 7/12
324/207.2
(Continued)

FOREIGN PATENT DOCUMENTS

WO WO-2016/057033 A1 4/2016

OTHER PUBLICATIONS

"International Application Serial No. PCT/US2014/059738, International Search Report mailed Jun. 29, 2015", 3 pgs.
(Continued)

*Primary Examiner* — Jermele M Hollington
*Assistant Examiner* — Christopher McAndrew
(74) *Attorney, Agent, or Firm* — Gilliam IP PLLC

(57) ABSTRACT

An apparatus and method provides for nondestructive inspection of a generally tubular target structure (such as a wellbore casing) by rolling contact engagement of one or more rolling probe devices with the target structure. Each rolling probe device carries electromagnetic (EM) measurement instrumentation to capture measurement data during rolling contact engagement with the casing. Each rolling probe device may comprise an instrumentation carrier (e.g., a roller or a wheel) having an endless tread surface to engage the target structure, with the EM measurement instrumentation extending along the endless tread surface and being located at or adjacent an exterior of the instrumentation carrier. A plurality of such rolling instrumentation carriers can be mounted at azimuthally spaced positions on a tool body configured for axial movement along a wellbore.

20 Claims, 12 Drawing Sheets

(51) Int. Cl.
*E21B 47/01* (2012.01)
*E21B 47/10* (2012.01)
*G01V 3/26* (2006.01)
*G01V 3/12* (2006.01)
*G01V 1/00* (2006.01)
*G01V 3/08* (2006.01)
*E21B 47/12* (2012.01)

(52) U.S. Cl.
CPC ............ *E21B 47/01* (2013.01); *E21B 47/102* (2013.01); *G01V 3/26* (2013.01); *E21B 47/122* (2013.01); *G01V 1/008* (2013.01); *G01V 3/082* (2013.01); *G01V 3/12* (2013.01)

(58) Field of Classification Search
USPC ......................................................... 324/344
See application file for complete search history.

(56) References Cited

U.S. PATENT DOCUMENTS

| | | | | |
|---|---|---|---|---|
| 3,922,015 A * | 11/1975 | Poundstone | ............ | E21C 35/24 175/50 |
| 4,292,589 A | 9/1981 | Bonner et al. | | |
| 4,646,240 A * | 2/1987 | Serra | ................... | G01V 11/002 324/323 |
| 5,532,587 A | 7/1996 | Downs et al. | | |
| 5,565,633 A | 10/1996 | Wernicke | | |
| 6,100,684 A | 8/2000 | Ramaut | | |
| 7,178,627 B2 * | 2/2007 | West | ..................... | G01V 1/40 181/105 |
| 7,289,909 B2 * | 10/2007 | Thomann | ................. | G01V 1/50 702/6 |
| 7,595,636 B2 | 9/2009 | Barolak et al. | | |
| 7,669,668 B2 * | 3/2010 | Martinez | ................. | E21B 47/08 175/40 |
| 7,677,314 B2 * | 3/2010 | Hsu | .......................... | C10G 1/02 166/302 |
| 8,210,251 B2 * | 7/2012 | Lynde | ..................... | E21B 23/14 166/55.7 |
| 2004/0100256 A1 | 5/2004 | Fickert et al. | | |
| 2008/0218170 A1 * | 9/2008 | Stolarczyk | ............... | G01V 3/17 324/330 |
| 2009/0039889 A1 * | 2/2009 | Wilt | ......................... | G01V 3/30 324/338 |
| 2009/0101337 A1 | 4/2009 | Neidhardt | | |
| 2010/0258297 A1 * | 10/2010 | Lynde | ..................... | E21B 37/00 166/105.1 |
| 2010/0258298 A1 * | 10/2010 | Lynde | ..................... | E21B 37/02 166/173 |
| 2010/0263856 A1 * | 10/2010 | Lynde | ..................... | E21B 23/14 166/53 |
| 2012/0062223 A1 * | 3/2012 | Olsson | ................... | G01R 33/10 324/252 |
| 2013/0068479 A1 * | 3/2013 | AlDossary | .............. | E21B 23/14 166/381 |
| 2013/0081875 A1 * | 4/2013 | Hyde | ...................... | E21B 23/14 175/17 |
| 2013/0275099 A1 * | 10/2013 | Frydman | ............. | G06F 17/5009 703/2 |

OTHER PUBLICATIONS

"International Application Serial No. PCT/US2014/059738, Written Opinion mailed Jun. 29, 2015", 4 pgs.

Edwards, J. M., et al., "Field results of the electromagnetic casing inspection log", SPE 664, *Journal of Petroleum Technology*, 16(4), (1964), 377-382.

Rourke, Marvin, et al., "Multi-tubular corrosion inspection using a pulsed eddy current logging tool", *IPTC 16645, .International Petroleum Technology Conference*, Mar. 26-28, Beijing, China, (2013), 1-6.

Vogtsberger, D. C., et al., "Development of high-resolution axial flux leakage casing-inspection tools", *SPE 97807, SPE Eastern Regional Meeting*, Sep. 14-16, 2005, Morgantown, West Virginia, (2005), 1-8.

* cited by examiner

ELECTROMAGNETIC IMAGING FOR STRUCTURAL INSPECTION

PRIORITY APPLICATIONS

This applications is a U.S. National Stage Filing under 35 U.S.C. §371 from International Application No. PCT/US2014/059738, filed on 8 Oct. 2014, which application is incorporated herein in its entirety.

TECHNICAL FIELD

The present application relates generally to nondestructive testing (NDT) using electromagnetic methods to inspect structures or structural elements, and more specifically to inspecting and monitoring structural properties of wellbore casings.

BACKGROUND

Wells drilled for hydrocarbon production may be completed by lining an inner surface of a wellbore with casing (also referred to as pipe or tubulars) of an impervious material, such as steel. A cased wellbore may improve control of pressure in the wellbore and direct the flow of liquids along the wellbore. For safety and environmental reasons, structural integrity of the casing is important.

During the life of a well, the casing is subject to degradation, for example due to corrosion and mechanical stress. Regular inspection and monitoring of the integrity of the casing may identify, before a failure event, when replacement or repair of the casing is necessary. Casing inspection is often performed using wireline-deployed tools capturing magnetic flux leakage (MFL) measurements or eddy current (EC) measurements that may be analyzed to provide an indication of testing integrity.

BRIEF DESCRIPTION OF THE DRAWINGS

Some embodiments are illustrated by way of example and not limitation in the figures of the accompanying drawings in which.

DETAILED DESCRIPTION

The following detailed description refers to the accompanying drawings that depict various details of examples selected to show how aspects of this disclosure may be practiced. The discussion addresses various examples of the inventive subject matter at least partially in reference to these drawings, and describes the depicted embodiments in sufficient detail to enable those skilled in the art to practice the subject matter disclosed herein. Many other embodiments may be utilized for practicing the inventive subject matter other than the illustrative examples discussed herein, and structural and operational changes in addition to the alternatives specifically discussed herein may be made without departing from the scope of the inventive subject matter.

In this description, references to "one embodiment" or "an embodiment," or to "one example" or "an example," are not intended necessarily to refer to the same embodiment or example; however, neither are such embodiments mutually exclusive, unless so stated or as will be readily apparent to those of ordinary skill in the art having the benefit of this disclosure. Thus, a variety of combinations and/or integrations of the embodiments and examples described herein may be included, as well as further embodiments and examples as defined within the scope of all claims based on this disclosure, and all legal equivalents of such claims.

An example embodiment of this disclosure comprises an apparatus and method for nondestructive inspection of a target structure (such as a wellbore casing) by rolling contact engagement of one or more rolling probe devices with the target structure, each rolling probe device carrying measurement instrumentation to capture electromagnetic measurement data during rolling contact engagement with the target structure.

In some embodiments, an apparatus for nondestructive structural inspection may comprise a tool body and one or more rolling probe assembly mounted on the tool body and configured for measuring one or more properties of the target structure during rolling contact engagement with the target structure. Each rolling probe assembly may comprise an instrumentation carrier (e.g., a roller) having an endless tread surface configured for rolling contact engagement with the target structure, and measurement instrumentation (e.g., transmitters and sensor antennae) extending along the endless tread surface, being located at or adjacent an exterior of the instrumentation carrier. As an alternative, some embodiments may include one or more instrumentation carriers and one or more rolling assemblies without an instrumentation carrier.

Figure 1:
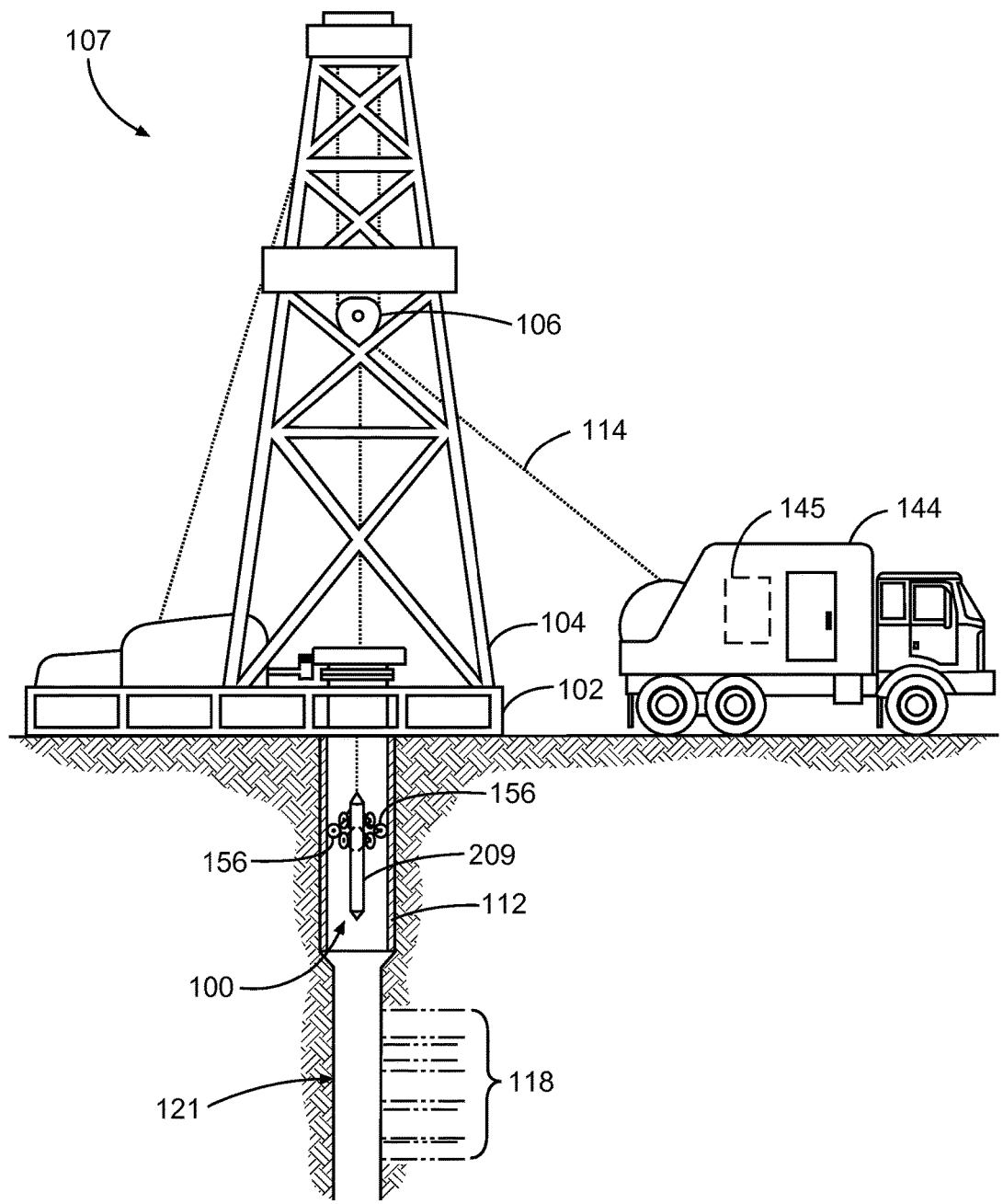
FIG. 1 is a schematic view of a system for, in a wireline logging operation, capturing electromagnetic measurement data for structural inspection of a wellbore casing, in accordance with an example embodiment.

FIG. 1 is a schematic illustration of a casing inspection tool 100 in accordance with an example embodiment deployed in an example well 107, in this instance being an oil well. The well 107 comprises a wellbore 121 that penetrates Earth formations 118 for the extraction of hydrocarbons from the Earth formations 118. The wellbore 121 is circular cylindrical, with a radially inner surface of the wellbore 121 along an upper part of its length being lined by a tubular steel casing 112. The casing 112 may have perforations along certain parts of its length, to allow ingress of hydrocarbons in liquid form into the wellbore 121, through the casing 112.

The casing inspection tool 100 is suspended from a drilling platform 102 equipped with a derrick 104 that supports a hoist 106 for raising and lowering the casing inspection tool 100. The casing inspection tool 100 in this example embodiment is a wireline tool, being suspended from the hoist 106 by a wireline 114 comprising a cable having conductors for conducting power to the casing inspection tool 100 from an aboveground logging facility 144, and for transmitting telemetry data (which may include electromagnetic measurement data) from the casing inspection tool 100 to the surface. Use of the wireline 114 enables controlled movement of the casing inspection tool 100 lengthwise along the casing 112, through the entire length of the casing 112. Note, however, that use of inspection tools consistent with this description is not limited to deployment as part of a wireline tool, as described below. Other embodiments may, for example, provide for deployment and use of inspection tools similar or analogous to the casing inspection tool 100 as part of a drillstring or by means of coiled tubing.

The casing inspection tool 100 can include a variety of sensors, including (as will be described in greater detail below) an electromagnetic (EM) sensor system for inspecting structural integrity of the casing 112. In this example embodiment, the EM sensor system comprises a plurality of rolling probe assemblies in the example form of roller assemblies 156 configured for rolling contact engagement with a radially inner surface of the casing 112 to measure one or more properties of the casing 112 indicative of its structural integrity. Further sensors forming part of the casing inspection tool 100 may include one or more depth sensors, in which case the system may be configured to log casing property measurements such that that are correlated to corresponding depth measurements. In this context, "depth" means an axial distance, measured along a central axis of the wellbore 121, from a wellhead at the surface.

Figure 7:
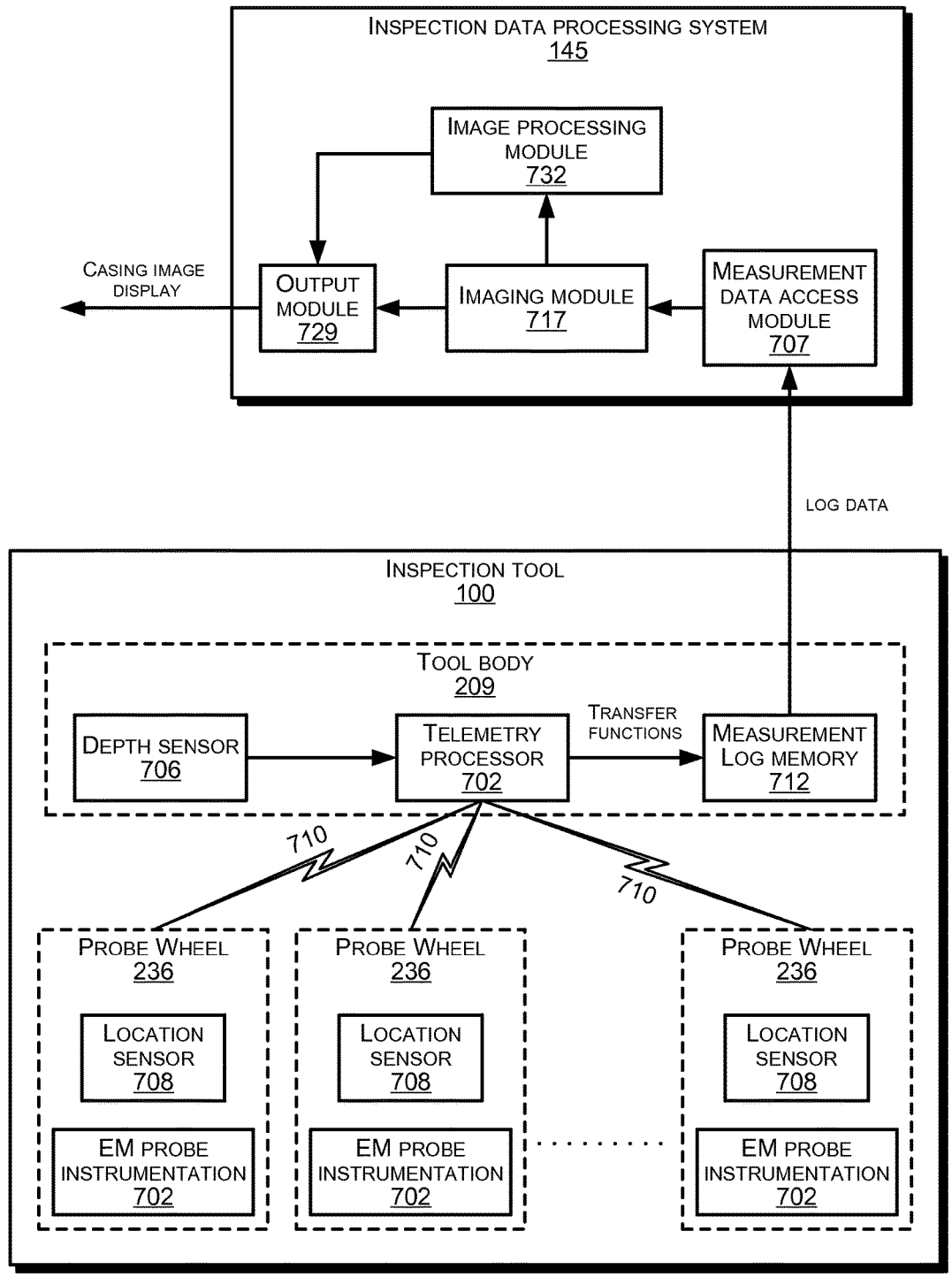
FIG. 7 is a schematic block diagram of a casing inspection system for nondestructive testing of structural properties of a wellbore casing, according to an example embodiment.

A surface logging facility 144 collects measurements from the casing inspection tool 100, and includes a computer-implemented inspection data processing system 145 for processing and storing the measurements gathered by the sensors (see, for example, FIG. 7). In some embodiments, the casing inspection tool 100 does not communicate with the surface in real-time, but rather stores logging data for later retrieval at the surface when the casing inspection tool 100 is recovered. Instead, or in addition, the tool 100 may be configured for downhole processing of measurement data. In such cases, electronic components providing at least some of the functionalities of the surface logging facility 144 and the processing system 145 (as described in the current example embodiment) may be incorporated in a body of the casing inspection tool, for movement with the roller assemblies 156 along the wellbore 121. Such downhole electronic components of the tool may be provided with electrical power from an onboard power source (such as a battery) housed by the tool 100. The downhole data processing components may be communicatively coupled to the roller assemblies 156 for receiving measurement data therefrom. In use, measurement data gathered by the roller assemblies 156 can be processed by these electronic components while the tool 100 is located downhole, in a manner similar or analogous to that described below with reference to the aboveground data processing system 145 and logging facility 144. In such embodiments, the tool may be configured to have data logging functionality for logging raw measurement data gathered by the roller assemblies 156 and/or for logging processed data generated by the downhole processing components based on the raw measurement data.

Figure 2:
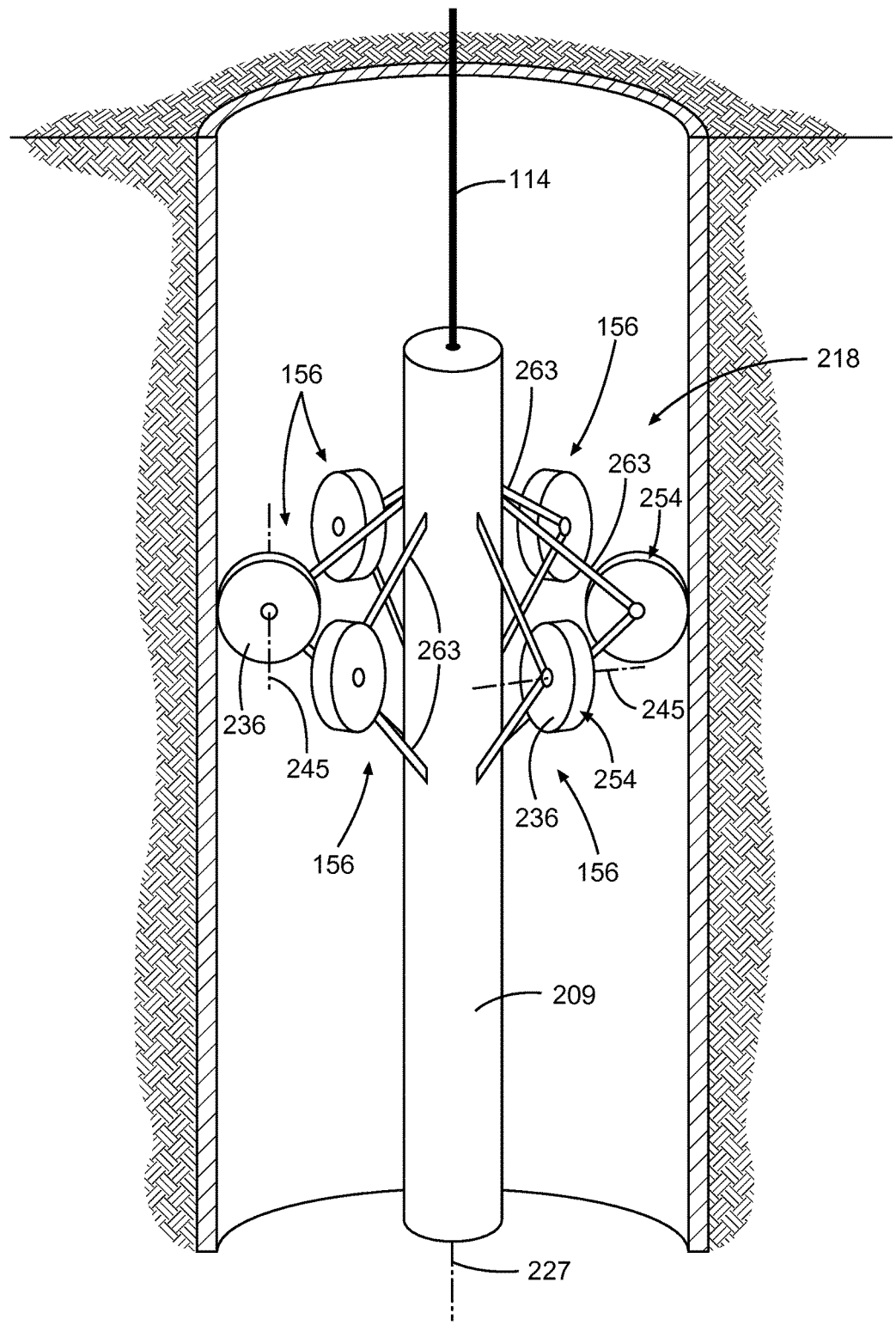
FIG. 2 is a schematic three-dimensional view of an inspection tool for capturing electromagnetic measurement data within a wellbore, in accordance with an example embodiment, the inspection tool being shown in rolling contact engagement with a wellbore casing, which is shown in partially sectioned three-dimensional view.

FIG. 2 shows a schematic view of the casing inspection tool 100, in accordance with an example embodiment. The casing inspection tool 100 comprises an elongated tool body 209 which is generally cylindrical and is sized and shaped for insertion in and movement lengthwise along the wellbore 121. In this example embodiment, the EM sensor system comprises a set 218 of six roller assemblies 156 located at a common axial position on the tool body 209 and arranged at a regular circumferential spacing about a longitudinal axis 227 of inspection tool 100, therefore being located at a regular azimuthal spacing in the wellbore 121. In the example embodiment of FIG. 2, an angular spacing between neighboring roller assemblies 156 is 60°.

Figure 3:
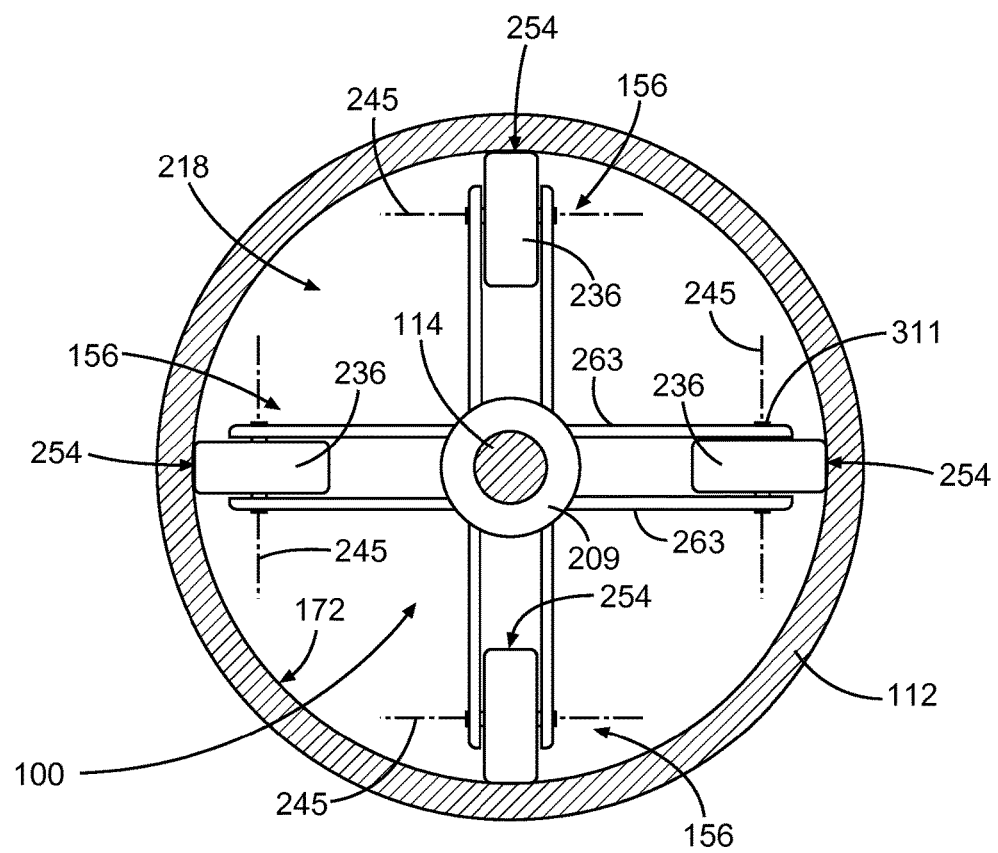
FIG. 3 is a schematic axial end view of a wellbore casing and an inspection tool for capturing electromagnetic measurement data indicative of structural properties of the wellbore casing, and accordance with an example embodiment.

Note, in other embodiments, the casing inspection tool can have a different number of roller assemblies 156 in a set. In embodiments with at least three roller assemblies 156 deployed from the same axial position of the tool body 209, the roller assemblies may provide stability for tool centralization. As an example, FIG. 3 illustrates an embodiment of a casing inspection tool that has a set 218 of four roller assemblies 156. For ease and clarity of description, similar and analogous elements are indicated by the same reference numerals in the embodiments of the FIGS. 2 and 3.

Each roller assembly 156 comprises a rotor in the example embodiment of a wheel 236 mounted for rotation relative to the tool body 209 about a respective rotational axis 245 that is transverse to (in this case being perpendicular to) the longitudinal axis 227 of the tool body 209. Further, each wheel 236 may carry measurement instrumentation for capturing inspection data indicative of one or more properties of the casing 112 when the wheel 236 is brought into rolling contact with the casing 112 during deployment of the casing inspection tool 100.

In some embodiments, less than all of the wheels 236 may carry measurement instrumentation. One or more of the wheels 236 may include alternative instrumentation and/or sensors. In addition, one or more of the wheels 236 may not include any instrumentation while still providing rolling contact and physical/mechanical support.

As will be described in greater detail below with reference to FIGS. 4A and 4B, the measurement instrumentation may comprise a plurality of transmitters and receivers deployed at or adjacent a radially outer tread surface 254 for electromagnetic inspection of structural properties of the casing 112 by inducing and measuring eddy currents in the casing 112.

Each wheel 236 is mounted on the tool body 209 by an undercarriage to allow controlled radial displacement of the wheel 236 relative to the longitudinal axis 227 of the tool body 209. In this example embodiment, each undercarriage comprises a pair of retractable arms 263 that are pivotally coupled at their distal ends to pivot about an axis co-axial with the rotational axis 245 of the corresponding wheel 236. Proximal ends of the arms 263 are pivotally connected to the tool body 209, with at least one of the proximal ends of the arms 263 of each undercarriage being axially slidable along the tool body. Each undercarriage is thus configured in this example embodiment for jackknife-fashion articulation to permit adjustment of radial spacing of the respective wheels 236 from the longitudinal axis 227 by variation of an included angle between the arms 263 of the associated undercarriage.

In some embodiments, the arms 263 of each undercarriage may be laterally spaced, to be located to opposite sides of the associated wheel 236 and being attached at their distal ends to a spindle 311 defining the rotational axis 245 of the wheel 236. In yet further embodiments, each of the arms 263 may comprise a pair of laterally spaced parallel bars flanking the corresponding wheel 236.

Figure 5:
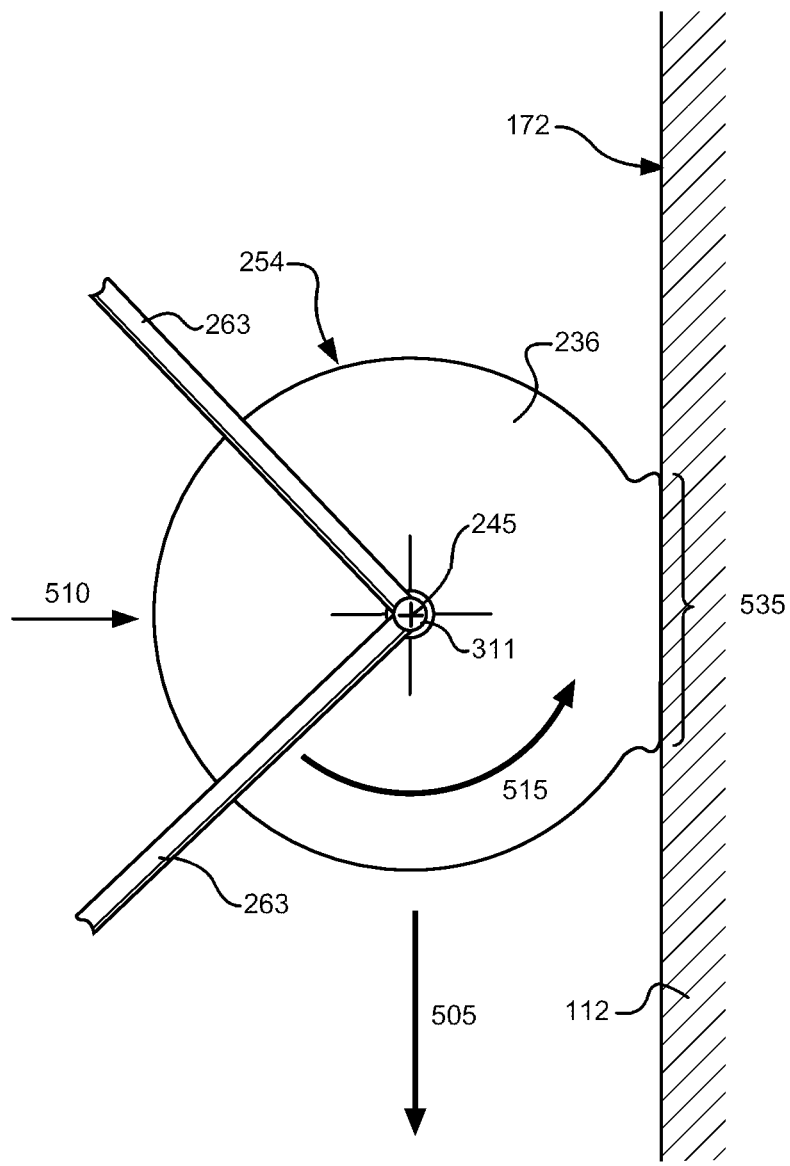
FIG. 5 is a schematic side view, of rolling contact engagement with a wellbore casing by a rolling probe forming part of a casing inspection tool, according to an example embodiment, with part of the wellbore casing being shown in axial section.

Each roller assembly 156 may comprise an urging mechanism for urging radial outward displacement of the corresponding wheel 236, to press the wheel 236 into contact with the casing surface 172 such as to cause deformation of the wheel 236 (as illustrated schematically in FIG. 5). In such an urging mechanism may comprise one or more helical compression springs mounted in cooperation with the expansion arms 263, to urge radially outward displacement of the associated wheel 236.

In other embodiments, the urging mechanism may include one or more servomotors operatively coupled to the suspension arms 263 to cause radially outward urging of the respective wheels 236. The suspension arms 263 of each undercarriage can, for example, be activated using mechanical and/or hydraulic controls, so that the wheels 236 are initially disposed in a retracted position in which the wheels 236 are radially withdraw relative to their positions illustrated in FIG. 2. In such case, radially outward displacement of the wheels 236, via the suspension arms 263 can be hydraulic mechanically or electronically actuated when the casing inspection tool 100 is axially in register with the casing 112, to press the wheels 236 radially outward against the casing surface 172 for capturing electromagnetic measurements, and to center the tool body 209 in the wellbore 121. When a measurement run (e.g., comprising ascent or descent of the tool body 209 along the length of the casing 112) is completed, the hydraulic or mechanical actuating mechanism may be operated to retract the wheels 236 radially inwards towards the tool body 209, to allow axially upward displacement of the tool body 209 along the wellbore 121 without engagement with the casing 112.

Such an urging mechanism serves not only to exert radially outward force (also referred to herein as downforce) on the respective wheels 236 to cause elasticity formation of the wheels 236 (as illustrated schematically in FIG. 5), but may additionally serve as a centering $^i$mechanism for centering the tool body 209 into the wellbore 121, such that the longitudinal axis 227 of the tool body 209 is co-axial with a lengthwise axis 253 wellbore 121.

Figure 4A:
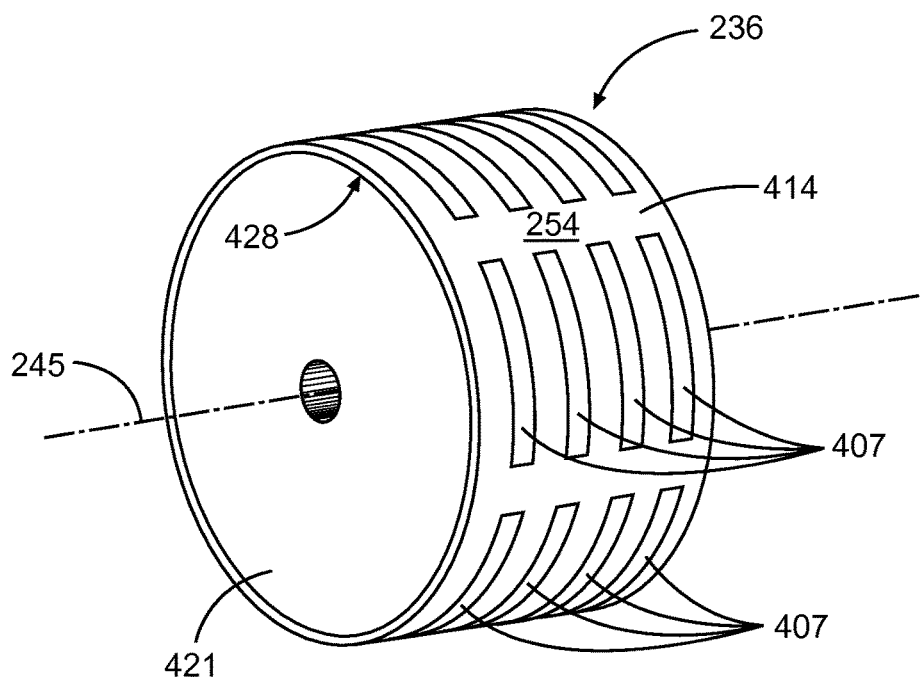
FIG. 4A and FIG. 4B are schematic three-dimensional views of a probe roller for forming part of a casing inspection tool, according to respective example embodiments.
Figure 4B:
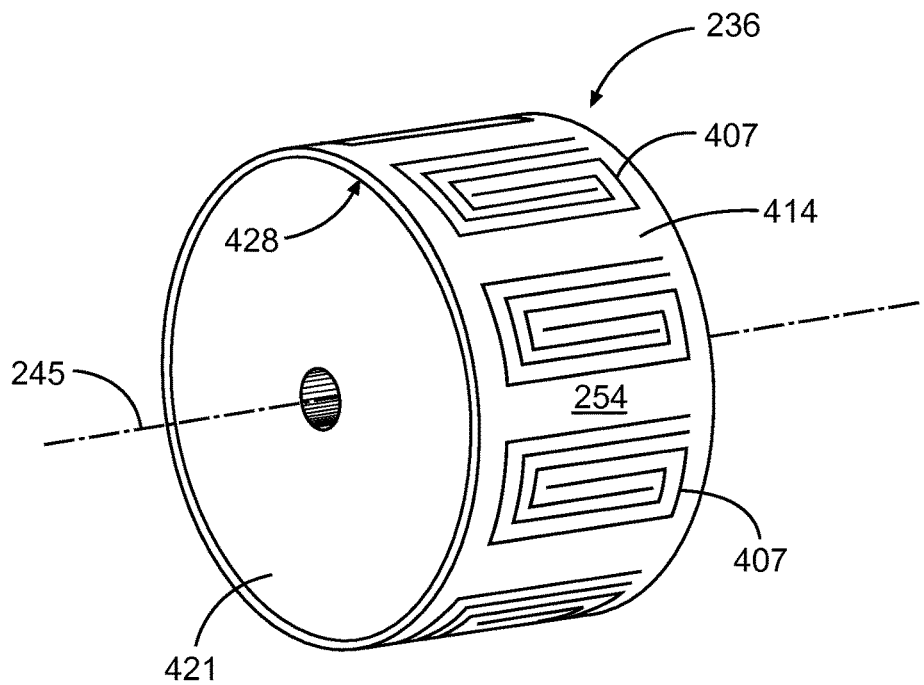

Two alternative example embodiments of the measurement instrumentation carried by the wheels 236 are shown in FIG. 4A and in FIG. 4B respectively. In the embodiment of FIG. 4A, a series of transmitters and receivers in the example form of microstrip antennae 407 are deployed on a high-temperature, flexible printed circuit board (PCB) 414. The wheel 236 comprises a solid cylindrical roller body 421 having a radially outer circumferentially extending surface that defines a cylindrical substrate surface 428 on which the PCB 414 is formed. The roller body 421 is of an elastically deformable material which is sufficiently soft to permit elastic deformation of the wheel 236 when it is pressed against the casing 112 by the arms 263 (see, e.g., FIG. 5). The radially outer surface of the PCB 414 therefore defines a radially outer tread surface 254 of the composite wheel 236 for bearing against a radially inner surface 172 (see FIG. 1) of the casing 112, for the referred to as the casing surface 172. The micro strip antennae 407 can be designed for inductive, galvanic, and/or capacitive sensing of structural properties of the casing 112. In other embodiments, the measurement instrumentation may comprise micro-electromechanical (MEMS) sensors.

In FIG. 4A, the wheel 236 is configured for capacitive EM sensing of structural properties of the casing 112, with the micro strip antennae 407 being positioned for capturing an impedance measurement due to capacitive coupling with the casing 112. In the example embodiment of FIG. 4B, however, the wheel 236 is configured for inductive EM inspection of the casing 112 with the micro strip antennae 407 positioned for an impedance measurement due to inductive coupling with the casing 112.

As shown in the example embodiments of FIG. 4, the flexible PCB 414 may be uncovered, so that a cylindrical radially outer surface of the PCB 414 defines the wheel's tread surface 254, which is in operation pressed against the casing surface 172 (see, e.g., FIG. 5). FIG. 5 shows an isolated view of rolling contact engagement between one of the wheels 236 and the casing 112. Radially outward urging of the wheels 236 via the suspension arms 263 presses the tread surface 254 into contact with the casing surface 172. If sufficient normal force (acting in direction 510) is applied to cause deformation of the wheel 236, a non-negligible part of the tread surface 254's circumference is flattened against the casing 112 (when seen in axial side view, such as in FIG. 5, or axial section). As a result of wheel deformation, a contact footprint of the wheel 236 on the casing surface 172 at any particular instant comprises an area spanning the width of the tread surface 254 and having an axial dimension (parallel to the longitudinal axis 227). In some embodiments, the axial dimension may vary between about 2 and 20 mm, in this example about 10 millimeters.

Each wheel 236 is, in this example embodiment, freely rotatable on the associated spindle 311 and can be mounted on the spindle 311 by a low friction mounting, such as a friction bearing or a rotor bearing. Exertion of the radially outward downforce (in direction 510) via suspension arms 263 causes not only the illustrated deformation of the wheel 236 at its interface with the casing surface 172, but also causes friction between the tread surface 254 and the casing surface 172 at the contact footprint 535 upon movement of the wheel axially along the wellbore 121. The resulting friction force may be sufficient to prevent slipping of the wheel 236 along the casing surface 172 and freewheeling rotation of the wheel 236 about the rotational axis 245. FIG. 5 schematically illustrates the movement of the casing inspection tool 100 (and therefore of the illustrated wheel 236) axially downwards along the wellbore 121, in direction 505, resulting in rotation of the wheel 236 about the rotational axis 245 in direction 515. Measurements may likewise be taken while the tool 100 is moved axially upwards of a wellbore 121, resulting in rotation of the wheel 236 in the rotational direction opposite to direction 515.

Such rolling contact engagement between the wheel 236 and the casing 112 provides uninterrupted migration of the wheel's contact footprint 535 along the casing surface 172 in an axially extending, substantially straight line. Because of the wheel's rolling movement, the micro antennae 407 on the tread surface 254 are cycled into and through the contact footprint 535. When a micro antenna 407 is in the contact footprint 535, the micro antenna 407 is stationary relative to the casing surface 172 and is at a constant, predictable spacing from the casing surface 172. In this example embodiment, the micro antenna 407 is shown pressed against the casing surface 172.

Figure 6:
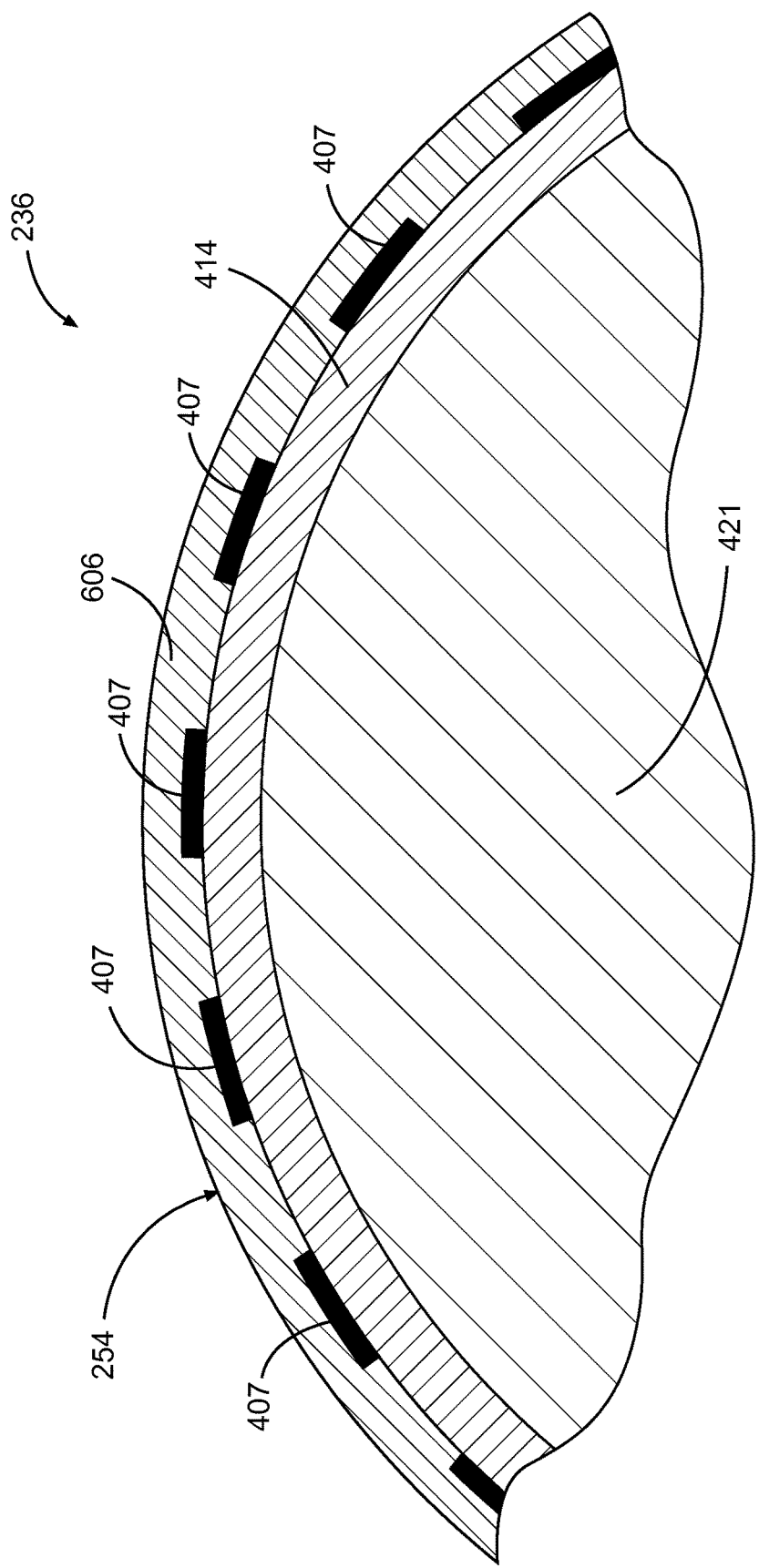
FIG. 6 is a schematic radial section of a part of a probe roller for a casing inspection tool, according to an example embodiment, the probe roller comprising a barrier layer that covers measurement instrumentation carried on a cylindrical substrate surface provided by a roller body, with a radially outer surface of the barrier later providing a tread surface for bearing against a wellbore casing.

FIG. 6 shows, on an enlarged scale, an axial section of a wheel 236 in accordance with another example embodiment. The wheel 236 of FIG. 6 is analogous in construction to those described above with reference to FIGS. 4A and 4B, having a soft elastomeric roller body 421 (e.g., from soft rubber) surrounded on its radially outer surface by a high-temperature flexible PCB 414, with the measurement instrumentation in the example form of micro strip antennae 407 carried on the radially outer surface of the PCB 414. In the embodiment of FIG. 6, however, the PCB 414 does not form the tread surface 254 of the wheel 236. Instead, a chemically inert, electrically insulating barrier layer 606 covers at least the radially outer surface of the PCB 414, covering and protecting the measurement micro strip antennae 407. The barrier layer 606 is configured to provide not only chemical and mechanical protection to the components of the wheel 236 which it covers, but also provides electrical insulation for the electromagnetic sensors (in this embodiment, the microstrip antennae 407) of the wheel 236.

In the embodiment of FIG. 6, the tread surface 254 that bears, in operation, against the casing surface 172 is defined not by the radially outer surface of the PCB 414 (as is the case in the example embodiment of FIGS. 4A and 4B), but is instead defined by the radially outer surface of the barrier layer 606. The measurement instrumentation of the wheel 236 (in this example embodiment being provided by the microstrip antennae 407) is therefore not carried on the tread surface 254, but is carried at or adjacent the tread surface 254, being spaced therefrom by the thickness of the barrier layer 606. When the wheel 236 is pressed against the casing 112, the micro strip antennae 407 are positioned parallel and adjacent to the casing surface 172, being spaced from the casing surface 172 at a consistent spacing provided by the thickness of the barrier layer 606.

In this example embodiment, the barrier layer 606 comprises an elastically deformable polymeric plastic material having a consistent radial thickness of between about 0.05 and 3 mm, in this example embodiment being about 0.25 mm thick. Note that the rigidity of the barrier layer 606 (i.e., the resistance of the constituent material to elastic deformation) may be equal to or lower than the rigidity of the PCB 414, which, in turn, may be equal to or lower than the rigidity of the roller body 421. This configuration may prevent laminar separation of the layers from one another, and ameliorate stress fatigue of the barrier layer 606 and the PCB 414.

Electromagnetic inspection measurements indicative of structural properties of the casing 112 may be taken successively by the micro antennae 407. As described above, the micro antennae 407 may operate at a minimum standoff distance from the casing surface 172. In this context, "standoff distance" means a radial spacing (relative to the longitudinal axis 227) between the interior casing surface 172 at the relevant EM sensor, such as the microstrip antennae 407. In this example, the minimum standoff distance is attained for a respective microstrip antenna 407 when it coincides with the contact footprint 535. In instances where the wheel 236 includes a barrier layer 606 (see e.g., FIG. 6), the minimum standoff distance may be substantially equal to the thickness of the barrier layer 606. Note that certain types of measurements may be effective only if there is physical contact between the sensor and the casing. In such cases, either no barrier layer 606 is used, or the sensors and barrier layer are formed so that at least part of the sensors extrude out or emerge from the radially outer surface of the barrier layer 606 for making contact with the casing 112.

As mentioned earlier, such electromagnetic property measurements may comprise measurement of eddy currents induced in the casing 112 by inductive, galvanic, and/or capacitive interaction with instrumentation of the casing inspection tool 100. In this example embodiment, the measurement instrumentation provided by the micro strip antennae 407 are configured for inductive coupling with the casing 112, with both induction and measurement being achieved via the micro strip antennae 407 on the tread surface 254. In other embodiments, instrumentation to induce electromagnetic activity in the casing 112 may be carried separate from the wheels 236, for example being housed on the tool body 209. In such a case, the measurement instrumentation on the wheels 236 may serve only to measure electromagnetic properties of fields and currents induced in the casing 112 by a centrally housed induction device. The antenna systems provided by the microstrip antennae 407 may be operated with an a range of frequencies, for example from hertz to terahertz frequencies, to ensure sufficient sampling and redundancy to form casing images (see, for example, FIGS. 8 and 10) based on processing of measurement data captured by the antenna systems.

The casing inspection tool 100 may further comprise a power supply system configured to deliver electrical power to the measurement instrumentation (e.g., to the microstrip antennae 407) of each of the probe wheels 236. In some example embodiments, the power supply system may comprise a self-sufficient power supply incorporated in each respective probe wheel 236. In this example embodiment, energy self-sufficiency may be achieved with a power source (e.g., a chemical battery) housed in the roller body 421 of the probe wheel 236 and electrically coupled to the microstrip antennae 407. In another example embodiment, energy self-sufficiency may be achieved by incorporation of an energy harvesting mechanism in each probe wheel 236. A generator may, for example, be attached to the spindle 311 of the probe wheel 236. The generator may harvest kinetic energy caused by axial movement of the casing inspection tool 100 along the wellbore 121 (resulting in rotation of the wheel 236 relative to the suspension arms 263), to produce electrical energy.

Instead, or in addition, each of the probe wheels 236 may in some embodiments be fed by a central power supply, e.g. housed by the tool body 209 or routed via the wireline 114. Electrical power can in such cases be delivered from the tool body 209 to each probe wheel 236 via a rotational electrical socket that preserves electrical conductivity as the wheel 236 is rotated. Such a rotational electrical socket can, for example, be located at the spindle 311. In a further example embodiment, electrical power can be delivered to each of the probe wheels 236 via an optical medium. In such a case, electrical power can be delivered from a laser housed by the tool body 209 via an optical fiber and a coupled rotational optical socket that preserves optical connectivity as the wheel assemblies rotate. Light received at the wheel 236 via the optical fiber may be used to activate a photodiode which delivers power to antenna systems, such as the microstrip antennae 407.

Note that some embodiments may employ different combinations of the above-described power supply configurations.

It should be noted, also, that because the casing surface 172 is cylindrical in shape, elastic deformation of the wheel 236 allows uninterrupted surface contact for the entire width of the tread surface 254, even in instances where the tread surface 254 has a rectilinear profile in radial section (e.g., when the wheel 236 is sectioned in a section plane that includes both the rotational axis 245 and a radius of the wheel, the shape of the tread surface 254 in the section plan is a straight line). In some embodiments, the tread surface 254 may have a convexly curved or arcuate profile in a radial section. In some example embodiments, the tread surface 254 has a convex curvature, when viewed in radial section, that matches the curvature of the cylindrical casing surface, so that elastic compression of the wheel 236 is substantially constant across the width of the tread surface 254.

FIG. 7 is a schematic block diagram of some electronic components of a casing inspection system 700 provided by the casing inspection tool 100 and the above-ground inspection data processing system 145. Electronic equipment forming part of the casing inspection tool 100 may comprise EM probe instrumentation 702 deployed on each probe wheel 236. The EM probe instrumentation may capture electromagnetic measurements indicative of structural properties of the casing 112, (e.g., the corresponding microstrip antennae 407 (see, e.g., FIG. 4)).

The casing inspection tool 100 further comprises a telemetry processor 704 housed by the tool body 209 and configured for receiving raw measurement data from each of the probe wheels 236 via an electrical telemetry system that provides respective communication links 710 between the telemetry processor 704 and each of the probe wheels 236. In some embodiments, each communication link 710 can be provided by a wireless communication system, for example comprising a wireless transmitter on each of the probe wheels 236, communicatively coupled to a wireless receiver in the tool body 209. In other embodiments, measured in data may be communicated to the telemetry processor 704 via communication links 710 provided by an optical telemetry system. As mentioned earlier, the casing inspection tool 100 may in some embodiments include data processing devices or components housed by the tool body 209 and configured for downhole processing and logging of EM measurement data captured by the tool 100.

The casing inspection tool 100 may include one or more additional telemetry sensors to supplement the EM data with additional information, such as meshed depth, probe wheel number, and/or position information indicating the respective positions of the probe wheels 236 relative to the tool body 209. In this example embodiment, such additional telemetry sensors include a location sensor 708 incorporated in each of the probe wheels 236 and a depth sensor 706 housed by the casing inspection tool 100 and coupled to the telemetry processor 704. Each location sensor 708 may be configured to measure a radial distance between the probe wheel 236 and the tool body 209. It will be appreciated that, when the probe wheels 236 are pressed into contact with the casing surface 172, the radial spacing information for two or more of the probe wheels 236 can be used by the telemetry processor 704 to calculate one or more measured diameters of the casing 112 at a particular axial position.

Although the location sensors 708 are in this example embodiment shown as being incorporated in the respective probe wheels 236, different position sensing arrangements may be employed in other embodiments. In embodiments such as FIG. 2, wherein the suspension mechanism of each probe wheel 236 comprises a pair of pivotally connected suspension arms 263, radial spacing of a particular probe wheels 236 from the tool body 209 can be calculated based on measurement of an included angle of a triangle in which two sides are defined by the suspension arms 263. In embodiments where the probe wheels 236 are azimuthally displaceable relative to the tool body 209, a location sensing arrangement may be configured to measure not only radial spacing of the probe wheels 236, but also to measure the azimuthal position of the respective probe wheels 236.

The telemetry processor 704 may be configured to process the received EM measurement data from the probe wheels 236 to a transfer function for each probe wheel 236. The transfer function is chosen such that it is sensitive to variations in the measured EM data caused by variations in physical properties of the steel casing 112. The physical properties of the casing 112 to which the measured EM data and the selected transfer function is sensitive in this example embodiment include variations in conductivity, permeability, and/or thickness of the casing 112, which may be caused by, for example, fractures, corrosion, pitting, gauging, or other phenomena that may compromise structural integrity of the casing 112. In some embodiments, the transfer function includes compensation, so as to obviate system calibration.

It will be appreciated that the EM probe instrumentation 702 (e.g., comprising the transmitter and receiver antennae 407 described with reference to FIG. 4) may comprise transmitters causing EM excitation measured by the co-located or adjacent sensors or receivers forming part of the EM probe instrumentation. The transmitters and sensors can be configured in different embodiments for different types of EM measurement. For example, the transmitters forming part of the EM probe instrumentation can be inductive (e.g., comprising coils), capacitive (e.g., comprising microstrips), and/or galvanic (e.g., comprising electrodes). The EM probe instrumentation 702 can further comprise a signal generator (e.g., a voltage controlled oscillator) to generate a current waveform (e.g., time-harmonic or pulse) for exciting the transmitter. In operation, an excitation signal can thus be transmitted by exciting the transmitters with a current waveform from the signal generator.

Likewise, the sensors or receivers forming part of the EM probe instrumentation 702 can be inductive (e.g., coils configured for measuring magnetic induction), capacitive (e.g., microstrips configured for measuring voltage), and/or galvanic (e.g., electrodes configured for measuring voltage). The EM probe instrumentation 702 may further comprise an electrical circuit formed in part by the EM sensors carried by the probe wheels 236. The electrical circuit may further include an amplification mechanism, e.g., a high impedance amplifier.

The EM probe instrumentation 702 in this example embodiment is configured to normalize received signals (e.g., voltages captured by the sensors) by the transmitted signals (e.g., current) and to produce the transfer function (e.g., impedance). In operation, the capture of EM measurement data with EM probe instrumentation 702 can thus comprise using signals transmitted via the transmitters to normalize signals received by the sensors or receivers and to, thereby, produce the transfer function.

Note that the transfer function may be configured differently for different types of EM transmitter and receivers provided by the particular EM probe instrumentation 702. A transfer function used for EM measurements captured by microstrip antennae 407 configured for capacitive coupling (such as in FIG. 4A), may, for example, be different from a transfer function used for EM measurement captured by microstrip antennae 407 configured for inductive coupling (such as in FIG. 4B). In some embodiments, the casing inspection tool 100, or each probe wheel 236, may be configured to include a plurality of different types of EM sensors, with the telemetry processor 704 being configured to process the data and provide a transfer function sensitive to variations in both types of measurements.

The telemetry processor 704 is in this example embodiment configured to write log data comprising depth-correlated transfer function values to a measurement log memory 712 housed by the tool body 209. The log data thus comprises an axial transfer function for each of the probe wheels 236. In this example, the log data is transferred from the onboard measurement log memory 712 to the above surface inspection data processing system 145 via a measurement data access module 707 forming part of the processing system 145 at the surface. Note that, in other embodiments the transfer function may be transmitted in real-time from the downhole casing inspection tool 100 to the surface processing system 145, to allow for real-time casing imaging.

The inspection data processing system 145 may include a hardware-implemented imaging module 717 configured to process the EM measurement data captured by the casing inspection tool 100 (e.g., represented by the transfer function), in order to estimate structural properties of the casing and to generate an output indicative of the estimated casing properties. In particular, the imaging module 717 is configured to assemble the plurality of measured transfer functions to form a casing image as a function of depth (axial position) and azimuthal orientation. The system 145 may further include an output module 729 configured to produce an operator-interpretable output of the estimated casing image generated by the imaging module 717.

In this example embodiment, the transfer function can be analyzed to retrieve casing property information. For example, transfer function impedance can be inverted to derive values for casing conductivity and/or permeability (or an apparent casing conductivity and/or permeability). These casing properties or apparent casing properties can subsequently be interpreted for identifying structural features, e.g., to identify the presence of corrosion. For example, the conductivity and permeability of iron oxides differ significantly from those of steel, so that corrosion may be inferred if the apparent casing conductivity and/or permeability deviates from acceptable tolerances. Generating a casing image can thus include (and the processing system 145 can be configured for) identifying areas of the casing for which measured values for apparent casing conductivity and/or permeability fall outside a predefined target range, and indicating the identified areas in the casing image as corroded areas.

Figure 10:
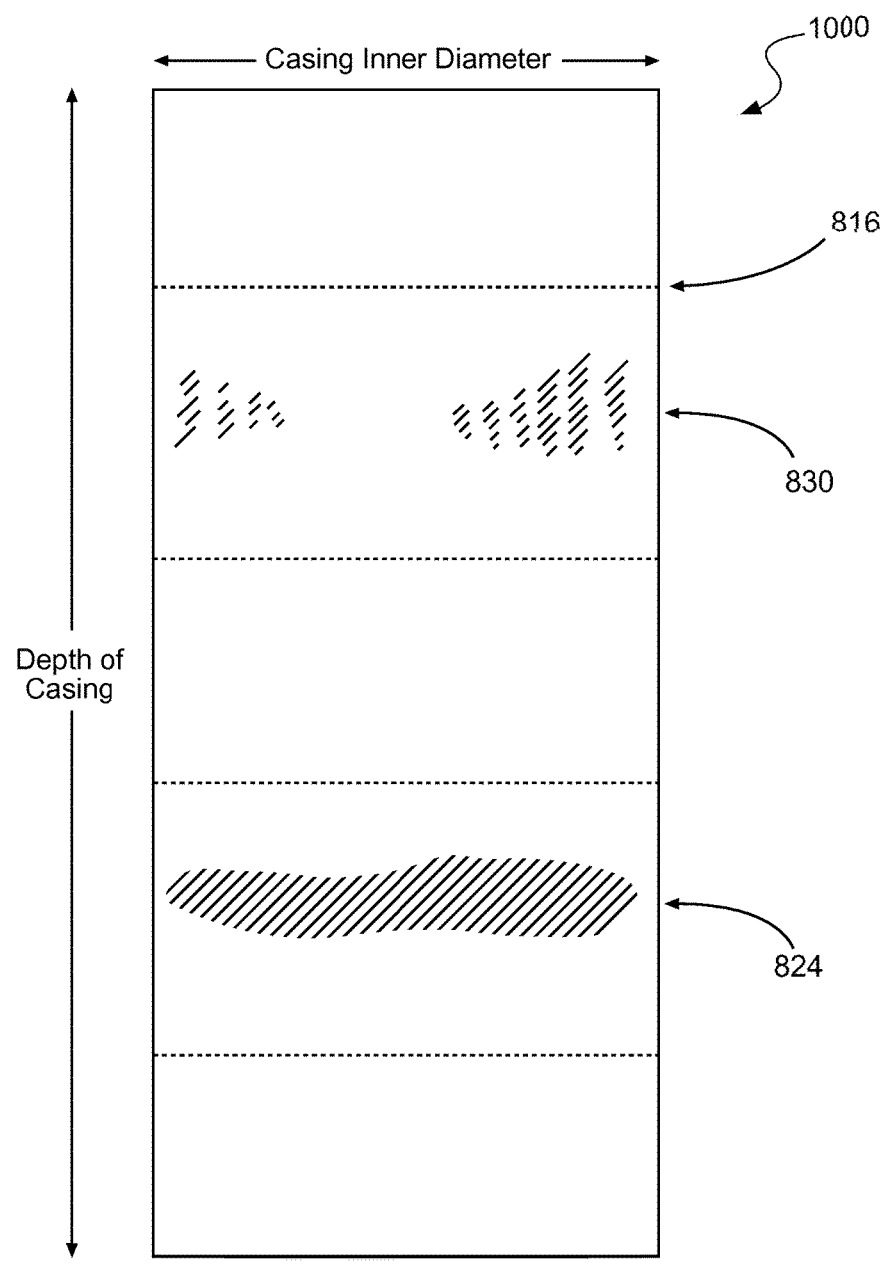
FIG. 10 is a schematic graph illustrating a 2-D casing image, according to an example embodiment, generated based on measurement data captured by a casing inspection tool providing for full azimuthal coverage of the casing's inner diameter.

Depending on the azimuthal distribution and the measurement width of relevant roller probes (in the example embodiment of FIG. 2 being provided by the probe wheels 236), the casing image provides partial azimuthal coverage of the casing 112 (FIG. 8) or full azimuthal coverage of the casing 112 (FIG. 10). If the casing 112 has no defects, the casing image will have no variation. If, however, the casing 112 has defects, the casing image will exhibit corresponding variations, which can be interpreted by an operator to identify integrity defects, such as fractures or corrosion. The casing image may include no structural features of the casing 112 are represented by variations in the axial transfer functions, such as case joints and ingress perforations through the casing 112. The casing image may in some examples be used for estimating perforation efficiency, for example by identifying perforation size, direction, and the like.

Figure 8:
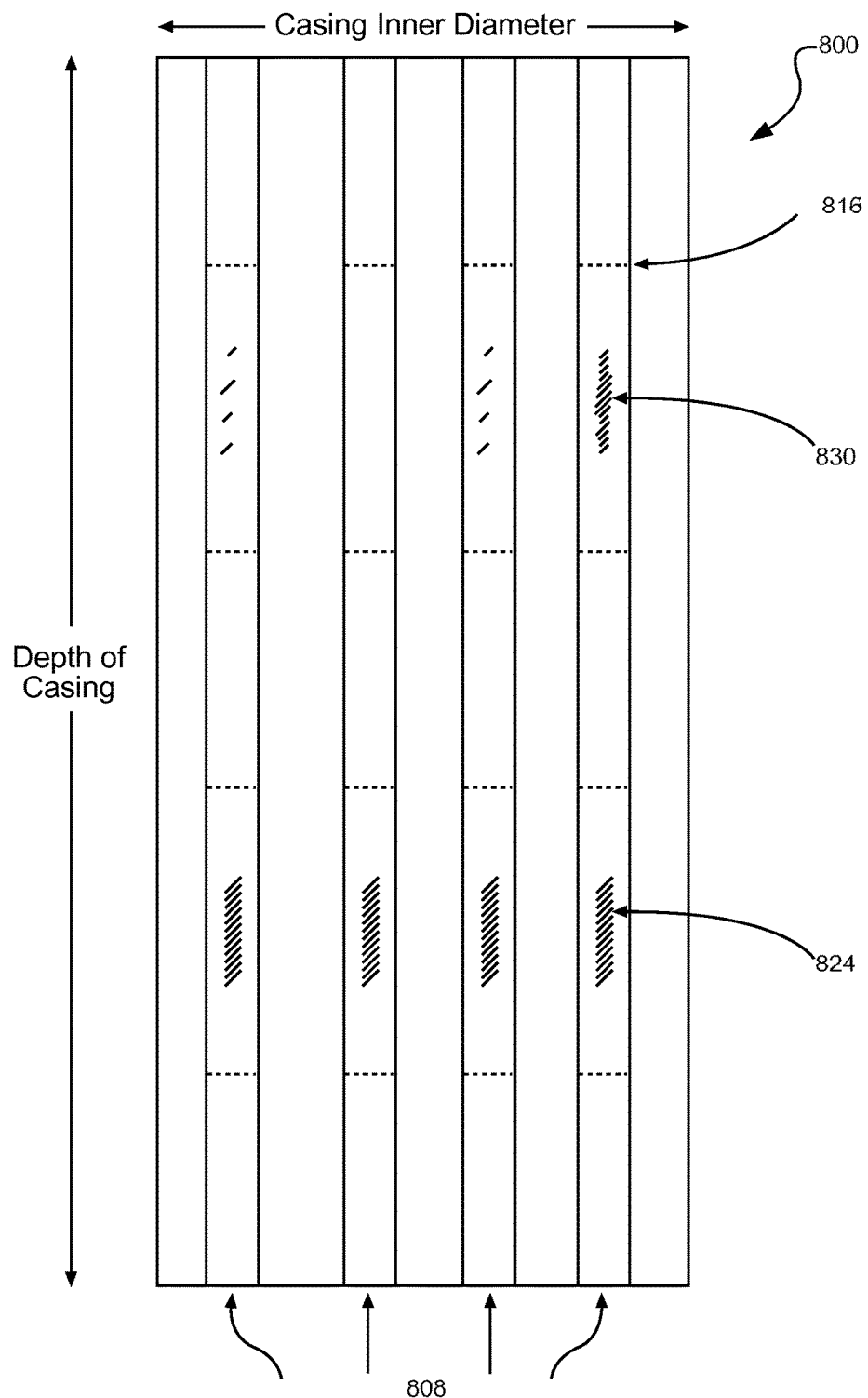
FIG. 8 is a schematic graph illustrating a 2-D casing image, according to an example embodiment, generated based on measurement data captured by a casing inspection tool such as that illustrated in FIG. 3.

FIG. 8 is a schematic view of an example casing image 800 that may be generated by the imaging module 717 and displayed on a graphic display screen, such as a computer monitor, by the output module 729. The casing image 800 in this example comprises a graphic 2-D image generated based on based on partial azimuthal coverage of the casing and the example four-wheel inspection tool 100. Note that the casing image 800 does not provide information about structural properties of the full azimuthal extent of the casing 112 (the azimuthal dimension of the casing 112 being oriented horizontally in FIG. 8), but instead provides information about structural properties of the casing 112 in four laterally spaced, axially extending tracks 808 corresponding to the respective wheels 236 of inspection tool 100.

Radially symmetrical features of the casing 112 are represented on all four of the tracks 808, at matching axial positions. For example, each casing joint 816 is indicated by matching horizontal lines extending across each of the tracks 808. Reference 824 in FIG. 8 likewise indicates symmetric corrosion 824, represented in the casing image 800 as a measured anomaly or feature that is present in all of the tracks 808 at a particular axial position, having substantially consistent properties across the tracks.

Non-symmetric structural features, however, can be identified based on differences between their manifestations on different tracks 808. For example, reference numeral 830 indicates measured structural features that represent non-symmetric corrosion of the casing 112 at the corresponding axial position, because measurements of the corrosion at that axial position manifests differently on the respective tracks 808. In this example, the nonsymmetric corrosion 830 is strongly indicated on the right-most track 808, and is wholly absent from the second track 808 (which represents measurements taken at an azimuthal position diametrically opposite that of the right-most track 808). It is also possible to generate an image based on measurement differences between a non-corroded section of the casing 112 or pipe (which may serve as a baseline measurement), and other sections of the casing 112 or pipe. A different baseline may be selected for different respective sections of the casing 112 or of the relevant measured pipe string. This is because different joints or sections tend to have different electrical characteristics, often display especially variability in magnetic permeability between different sections or joints.

Note that no data is provided for those parts of the casing image 800 located laterally between adjacent axial transfer function tracks 808. These azimuthal gaps in the casing image 800 results from azimuthal or circumferential spacing between neighboring wheels 236, as can be seen with reference to FIG. 3.

The inspection data processing system 145 in this example embodiment further includes an image processing module 732 configured for automated image processing of the casing image 800 (e.g., by applying predefined image processing algorithms to the casing image 800), thereby automatically to identify and characterize integrity defects indicated by respective features of the casing image 800. The image processing module 732 may further be configured to process multiple casing images 800 generated for the casing 112 based on measurements captured at staggered intervals, to automatically identify and characterize changes in respective integrity defects represented in the casing images 800. The image processing module 732 may, for example, be configured automatically to compare rates of change of respective defects, and to identify accelerated increase in any of the defects relative to the other defects. The imaging module 717 may likewise be configured to combine a plurality of time-staggered casing images 800, to produce an animated casing image that displays changes of the defects over time, for example comprising a time lapse video image.

In operation, the casing inspection tool 100 is inserted in the wellbore 121, with the rolling probe devices provided by the respective roller assemblies 156 being in a radially retracted mode in which the respective wheels 236 are located relative to the tool body at radii smaller than that of casing surface 172 defined by the inner diameter of the casing 112. Once inserted into the wellbore 121, the respective wheels 236 may automatically be extended radially outward by respective urging mechanisms incorporated in the undercarriages, so that each of the wheels 236 is pressed against the casing surface 172. Continues provision of such radial forces acting between the probe wheels 236 and the tool body 209 (via the respective undercarriages) promote substantially slip-free rolling contact engagement by the probe wheels 236 with the casing surface 172, and additionally serves as a centering mechanism for co-axial alignment of the tool body 209 with the longitudinal axis 227 of the casing 112.

Thereafter, the casing inspection tool 100 may be moved longitudinally along the casing 112 by raising or lowering the tool body 209 via the wireline 114. During such axial movement along the casing 112, each probe wheel 236 rolls along the casing surface 172 at a respective azimuthal position (see, e.g., FIG. 5), so that, at the contact interface between the probe wheel 236 and the casing 112 (schematically indicated in FIG. 5 as the contact footprint 535), there is substantially no relative movement between the radially outer tread surface 254 and the casing surface 172. EM measurement data in the example form of eddy current measurements are captured by the micro strip antennae 407 when they are successively rotated into the contact footprint 535 of the probe wheel 236. In embodiments where the probe wheels 236 have a barrier layer 606 such as that illustrated in FIG. 6, the measurement instrumentation provided by the microstrip antennae 407 are spaced from the casing surface 172 by a consistent standoff distance essentially equivalent to the thickness of the barrier layer 606, promoting consistent and reliable eddy current measurements.

Because the tread surface is endless, and because the series of microstrip antennae 407 extend along the tread surface in a substantially uninterrupted circumferentially extending series (e.g., being located on the tread surface when no barrier layer 606 is present, or below the tread surface 254 when a barrier layer 606 implied), each probe wheel 236 a substantially continuous series of EM measurements extending axially along the length of the casing 112 at a particular azimuthal position. These series of measurements can be processed as described with reference to FIGS. 7 and 8, to generate one or more casing images, automatically to identify structural defects, and/or to generate an animated representation of the casing illustrating variation of various casing features over a specific time interval spanned by a series of time-staggered data-gathering operations.

In one embodiment, the casing inspection tool 100 may be moved along the entire length of the casing 112 at a relatively high speed, to provide a relatively low-resolution casing image 800. Such an initial casing image 800 may be analyzed, e.g. by an operator or by automated image processing, to identify one or more areas of interest which are to be investigated in greater detail. The casing inspection tool 100 may thereafter be maneuvered towards a particular area of interest, after which the casing inspection tool 100 may be moved axially through the area of interest at a lower inspection speed, during which more reliable eddy current measurements are captured by the probe wheels 236. A more precise casing image 800 may thereafter be generated based on the secondary, more focused measurement session.

Various aspects discussed above with reference to system- and apparatus features apply mutatis mutandis to methods for electromagnetic inspection of target structures, such as the wellbore casing 112 described in the above example embodiments. Note also that, also the above example embodiments are described with reference to the inspection of a wellbore casing 112, the scope of this disclosure is not limited to wellbore applications. In inspection tool similar or analogous to that described with reference to the figures may, for example, employed for structural inspection of different tubular structures, such as service pipes.

Figure 9:
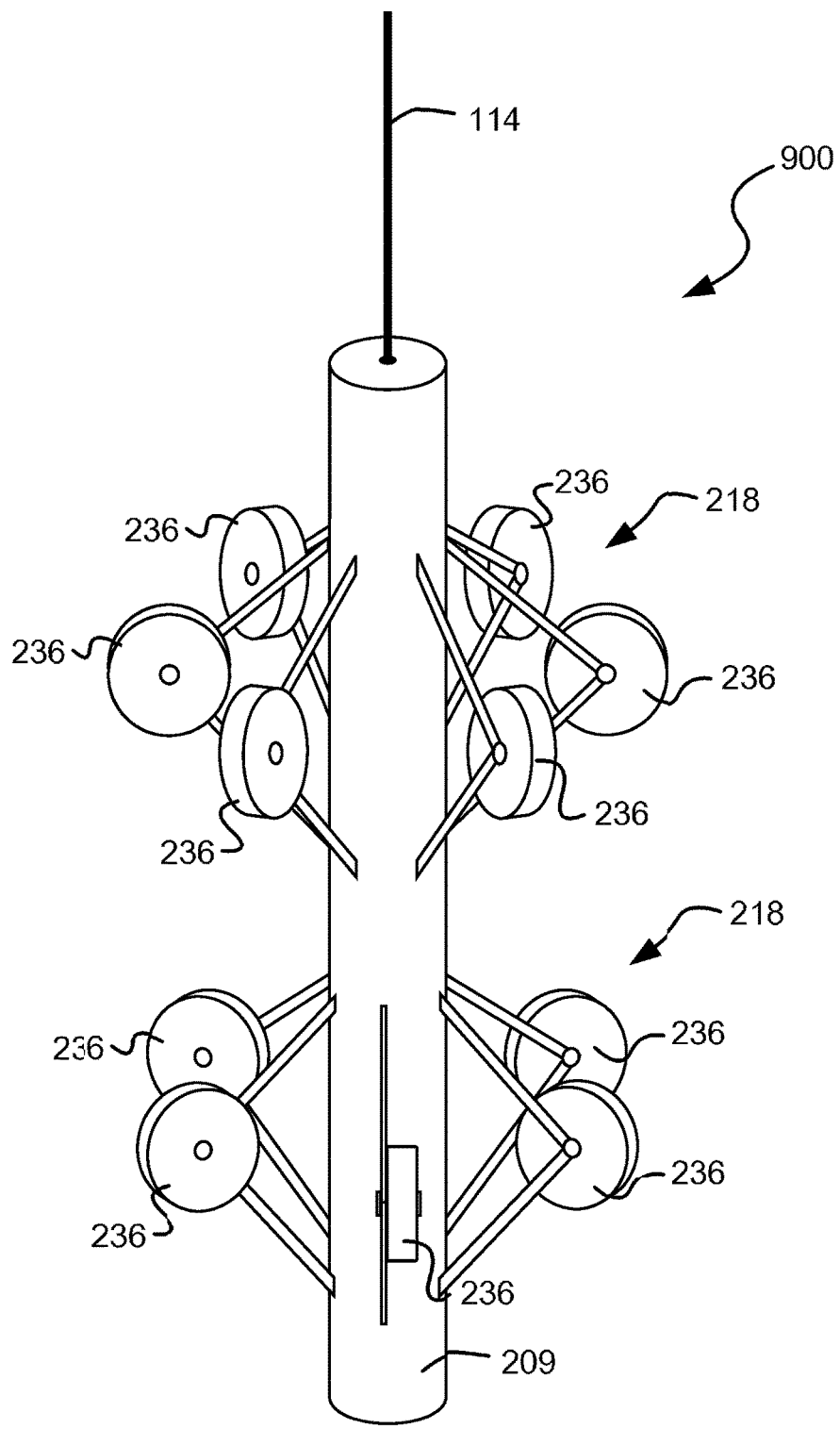
FIG. 9 is a schematic three-dimensional view of a casing inspection tool in accordance with another example embodiment, the casing inspection tool having two axially spaced sets of measurement wheel assemblies.

In some embodiments, greater azimuthal coverage (and in some embodiments, full azimuthal coverage) can be achieved by provision of two or more axially spaced sets 218 of roller assemblies 156. FIG. 9 illustrates one example embodiment of such a multiple-set inspection tool 900. The inspection tool 900 has a pair of roller assembly sets 218 spaced axially along the tool body 209. In the example embodiment of FIG. 9, both of the roller assembly sets 218 are identical to that described and illustrated with reference to the single-set inspection tool 100 of FIG. 2, with one of the roller assembly sets 218 being azimuthally rotated (i.e., angularly displaced about the longitudinal axis 227 of the tool body 209) relative to the other roller assembly sets 218, so that the wheels 236 of the respective sets 218 are misaligned. Here, each roller assembly set 218 has six wheels 236 spaced at a regular angular interval of 60°. The rotor assembly sets 218 are in this example misaligned by 30°, so that each wheel 236 of a lower one of the roller assembly sets 218 has an azimuthal position midway between a corresponding pair of wheels 236 of an upper one of the rotor assembly sets 218.

Casing imaging based inspection data gathered by the inspection tool 900 is based on logging data gathered cumulatively by both of the rotor assembly sets 218, thus providing structural integrity information for a greater portion of the casing's azimuthal extent than is the case for the comparative single-set inspection tool 100 of FIG. 2. As can be seen with reference to FIG. 9, the width of the individual wheels 236 of the multi-set inspection tool 900 of FIG. 9 is such that there are still gaps in the cumulative azimuthal coverage provided by the inspection tool 900. In other words, there is no circumferential overlap between neighboring wheels 236, when the inspection tool 900 is seen in axial end view (corresponding to the view of FIG. 3). A casing image generated based on data gathered by the inspection tool 900 would thus be analogous to the example casing image 800 of FIG. 8, except that it would consist of 12 laterally spaced axial transfer function tracks 808, with laterally adjacent tracts being separated by a lateral (i.e., azimuthal) gap smaller than is the case for the casing image 800 of FIG. 8.

In other embodiments, however, and inspection tool similar or analogous to that of FIG. 9 can be configured to provide full azimuthal coverage of the casing surface 172. This may be achieved, for example, by providing one or more additional sets 218 of roller assemblies 156, azimuthally unaligned with the gaps between azimuthally adjacent wheels 236 of inspection tool 900, FIG. 9. Instead, full azimuthal coverage may be achieved by and inspection tool that is similar in construction to the inspection tool 900 of FIG. 9, but with wheels 236 and that have a width greater than that illustrated in FIG. 9, so that the 12 wheels 236 of the inspection tool 900 fully cover the azimuthal extent of the casing surface 172.

FIG. 10 illustrates an example embodiment of a casing image 1000 that may be generated by the imaging module 717 based on measurement data gathered by and inspection tool that provides full azimuthal coverage. The example casing image 1000 of FIG. 10 is for the same example casing 112 for which the casing image 800 of FIG. 8 is generated. As can be seen in FIG. 10, the casing image 1000 has no azimuthal interruptions (i.e., being providing continuous information about structural properties of the casing 112), being generated based on electromagnetic inspection by respective wheels 236 for the entire azimuthal extent and the entire axial extent of the casing 112.

Figure 11:
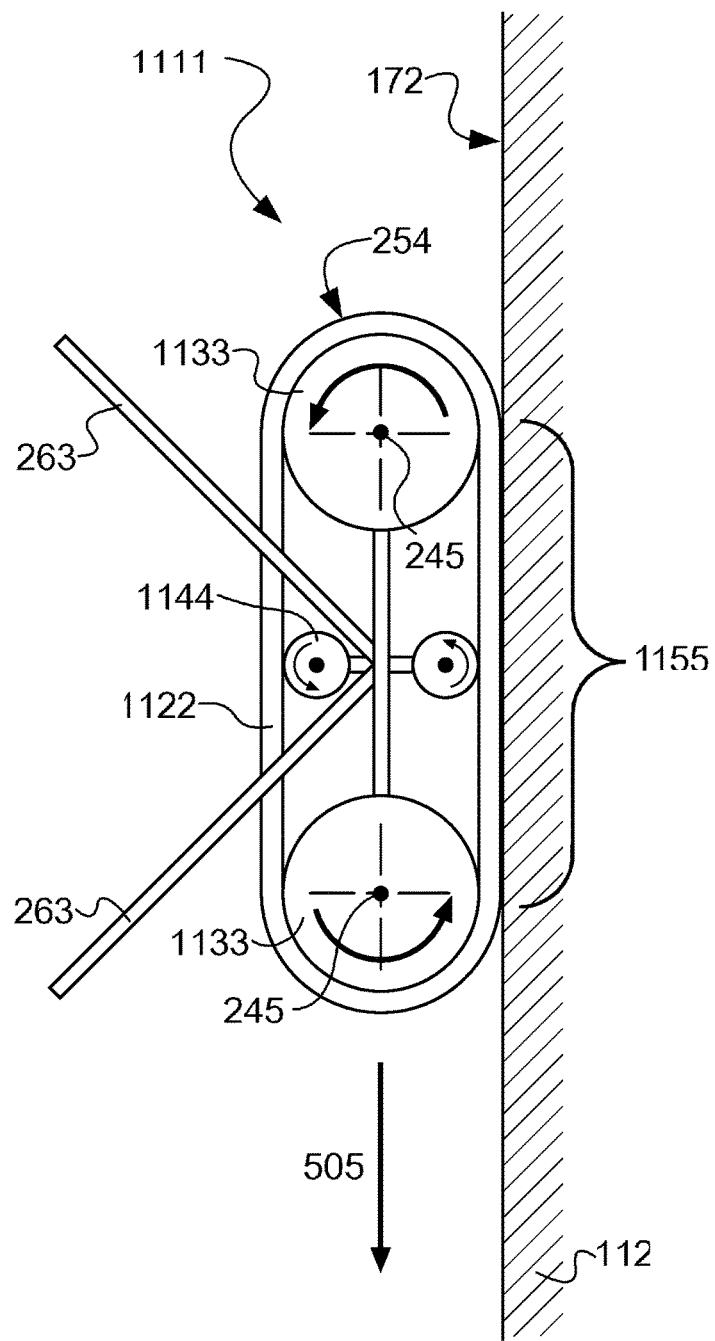
FIG. 11 is a schematic three-dimensional view of a rolling probe device for forming part of a casing inspection tool in accordance with another example embodiment, the rolling probe device being shown in rolling contact engagement with a wellbore casing, the casing being shown partially and in axial section.

It will be appreciated that rolling contact engagement between an electromagnetic measurement instrumentation carrier and the casing surface 172 may be achieved using structural configurations different from that described above with reference to FIGS. 1-9. One example embodiment of such an current instructional configuration is illustrated in FIG. 11, in which each roller assembly 156 comprises a track assembly 1111. The track assembly 1111 comprises an endless track 1122 that serves as an instrumentation carrier, with the endless track 1122 being rotatably movable in an endless loop about a pair of axially spaced guide wheels 1133. Each guide wheel is freely rotatable about a respective rotational axis 245 that is oriented tangentially relative to the longitudinal axis 227 of the tool body 209, and is urged radially into with the casing 112 by a suspension system or undercarriage similar to that described with reference to FIGS. 1-5. The track assembly 1111 further comprises a pair of tension wheels 1144 rotatable about respective axes parallel to the rotational axes of the guide wheels 1133, and positioned to limit slack in the endless track 1122, ensuring continuous contact between the endless track 1122 and the casing surface 172 along the entire length of the axial spacing between the guide wheels 1133.

The endless track 1122 in the second example embodiment comprises a high-temperature flexible printed circuit board similar in configuration to the PCB 414 of FIGS. 4 and 6, carrying measurement instrumentation (such as microstrip antennae 407) at or adjacent its radially outer surface, which outer surface defines a tread surface 254 for the track assembly 1111. In some embodiments, the tread surface 254 may be provided by and exposed outer surface of a PCB substrate of the endless track 1122 (similar to the configurations described with reference to FIGS. 4A and 4B), while, in other embodiments, the endless track 1122 may be a composite laminar structure that includes a flexible high-temperature PCB covered by a chemically inert, electrically insulated barrier layer, similar to the barrier layer 606 described with reference to FIG. 6.

In operation, the track assembly 1111 of FIG. 11 functions in a manner similar to the wheel assemblies 156 of FIGS. 2-10, but with a relatively larger contact footprint 1155 that substantially coincides with an axial spacing between the rotational axes of the guide wheels 1133. Note further that, unlike the wheel 236 of FIG. 5, area contact (as opposed to line contact) between the endless track 1122 of FIG. 11 is not dependent on elastic the formation of the guide wheels 1133, so that the guide wheels 1133 may in some embodiments be of a material that is relatively more resistant to deformation (i.e., being harder), than is the case for the wheels 236 described with reference to FIGS. 1-9.

It is a benefit of the example inspection tools and methods for casing inspection described above that it provides for a stable standoff distance between the measurement instrumentation (e.g., the microstrip antennae 407) and the casing 112, thereby providing improved signal-to-noise ratios. This is particularly advantageous for the inspection of nonmagnetic materials. Reliable signal processing is also facilitated by achieving a constant, known in standoff between the measurement instrumentation and the casing surface 172. Yet further, improved measurement sensitivity and accuracy are achieved by the relatively small standoff that between the rotor-Detroit measurement instrumentation and the casing 112.

A further benefit is that logging efficiencies can be improved by providing for wheel-deployed or track-deployed transmitters and receivers. Yet a further benefit is that, due to rolling contact engagement with the casing 112, the described inspection tools provide full substantially frictionless interaction with the casing, and therefore experiences and/or causes minimal mechanical degradation, when compared to add-type inspection devices that make sliding contact with the casing.

It is also a benefit of the described apparatuses and methods that it provides for the generation of casing images that are azimuthally variant, providing the ability accurately to represent non-symmetrical structural properties and/or features of the casing 112. Some embodiments provide for full azimuthal coverage, achieving a more comprehensive and complete casing image for more accurately informing maintenance decisions regarding the casing 112.

Although the disclosed material has been described with reference to specific example embodiments, various modifications and changes may be made to these embodiments without departing from the broader scope of the disclosure. Accordingly, the specification and drawings are to be regarded in an illustrative rather than a restrictive sense.

For example, in other embodiments may comprise an inspection tool analogous to those described above with reference to the drawings, but with the probe wheels 236 being azimuthally rotatable relative to the tool body 209. Referring to FIG. 2 or FIG. 9, it will be appreciated that such azimuthal rotation comprises angular displacement of the probe wheels 236 about the longitudinal axis 227 of the tool body 209. Each of the roller assemblies 156 can, for example, be mounted on a common sheath or collar mounted on the tool body 209 for driven rotation (e.g., driven by a motor housed by the tool body 209) relative to the tool body 209 about the longitudinal axis 227. Such driven azimuthal rotation of the probe wheels 236 during axial displacement of the tool body 209 along the wellbore 121 results in each probe wheels 236 describing a helical path along the interior casing surface 172.

It will be appreciated that each probe wheel 236 may in such a case be oriented for rolling along its helical paths, and/or may have a swivel mounting to dynamically correct its orientation, caster-fashion, responsive to axial and/or azimuthal displacement imparted to the probe wheel 236 via the tool body 209 and the suspension system by which it is mounted on the tool body 209. In another embodiment, the inspection tool may have a plurality of spherical rollers that provide respective rolling instrumentation carriers, instead of (or in addition to) substantially cylindrical wheels 236 as described, for example, with reference to FIG. 2. Such spherical rollers may be configured for free rotation about a dynamically variable axis intersecting the center of this spherical roller, for example having a ball-and-socket mounting on the undercarriage.

In yet a further embodiment, instrumentation carriers configured for rolling contact engagement with the casing 112 (such as, for example, probe wheels 236 such as an FIG. 2, and endless track 1122 such as in FIG. 7, or spherical rollers as described above) can be configured for driven displacement relative to the tool body both azimuthally (i.e., circumferentially relative to the longitudinal axis 227) and axially (i.e., parallel to the longitudinal axis 227). Such driven displacement may be remotely controllable by an operator, for example allowing an operator manning a real-time casing image to manipulate the roller probe assemblies 156 to any particular azimuthal and/or axial position on the interior casing surface 172. Due to axial stress ability of the roller probe assemblies 156 relative to the tool body 209, such controlled manipulation can be achieved without raising or lowering the tool body 209 via the wireline 114, if the position of interest coincides axially with substantially any part of the tool body 209.

Thus it will be seen that one aspect of the above-described example embodiments comprises an apparatus for nondestructive structural inspection, the apparatus comprising:
a tool body; and
one or more rolling probe assemblies mounted on the tool body and configured to measure one or more properties of a target structure, each rolling probe assembly comprising:
  an instrumentation carrier configured for revolving movement relative to the tool body when an endless tread surface defined by the instrumentation carrier bears against the target structure, to allow rolling contact engagement of endless tread surface with the target structure; and
  measuring instrumentation extending along the endless tread surface at or adjacent an exterior of the instrumentation carrier, the measuring instrumentation being configured for capturing electromagnetic measurement data during rolling contact engagement of the tread surface with the target structure, the electromagnetic measurement data being indicative of the one or more properties of the target structure.

In some embodiments, each instrumentation carrier of the one or more rolling probe assemblies comprises a roller that is rotatably mounted on the tool body about a respective axis of rotation, the endless tread surface being defined by a radially outer surface of the roller. Each roller may be of a roller is of a resiliently compressible material, each rolling probe assembly further comprising an urging mechanism for urging the corresponding roller into contact with the target structure such that a contact interface between the roller and the target structure comprises a substantially nonlinear area.

Each roller may comprise a roller body that defines an endless, circumferentially extending substrate surface, the measurement instrumentation comprising printed electronic circuitry carried on the substrate surface. In some embodiments, the measuring instrumentation may comprise a flexible printed circuit board mounted on the substrate surface.

The measuring instrumentation may comprise a substantially uninterrupted, regularly spaced series of sensor antennae, the series extending circumferentially along the tread surface of the roller.

In some embodiments, each instrumentation carrier may comprise:
a carrier body that defines a substrate surface on which the measurement instrumentation is carried; and
a barrier layer that covers the substrate surface and the measurement instrumentation such that the tread surface of the instrumentation carrier is defined by an outer surface of the barrier layer, the measurement instrumentation being located beneath the tread surface.

Each instrumentation carrier may comprise a flexible endless web, each rolling probe assembly further comprising a guide arrangement having two or more guide wheels rotatable about parallel, spaced rotational axes, the endless web being mounted on the guide arrangement for guided revolving movement about the two or more guide wheels in an endless loop.

The apparatus may be configured to measure the one or more properties of the target structure by rolling contact engagement with an interior cylindrical surface of the target structure, the tool body being configured for movement along a longitudinal axis of the interior cylindrical surface, and the one or more rolling probe assemblies comprising a plurality of rolling probe assemblies that are circumferentially spaced about the tool body for simultaneous rolling contact engagement with the interior cylindrical surface at different circumferential positions. In such cases, the tool body may be elongate, to extend lengthwise along the longitudinal axis of the interior cylindrical surface, and the plurality of rolling probe assemblies may be arranged in two or more axially spaced sets of rolling probe assemblies, each set of rolling probe assemblies comprising two or more circumferentially spaced, axially aligned rolling probe assemblies.

The two or more sets of rolling probe assemblies may be substantially identical in spatial arrangement, but while being angularly displaced relative to each other, so that the instrumentation carriers of the rolling probe assemblies of respective sets are axially misaligned. The plurality of rolling probe assemblies, when seen in axial end view, may cumulatively provide full circumferential coverage of the interior cylindrical surface of the target structure.

Each rolling probe assembly may comprise an undercarriage that mounts the associated instrumentation carrier on the tool body such that a radial spacing between the tool body and the instrumentation carrier, relative to the longitudinal axis, is dynamically variable. In such cases, each rolling probe assembly may comprise and urging mechanism configured to urge the associated instrumentation carrier radially outwards and into contact with the interior cylindrical surface.

In some embodiments, the apparatus may be configured for electromagnetic inspection of a wellbore casing, the tool body being configured for insertion in and lengthwise movement along the wellbore casing. In other embodiments, the apparatus may be configured for electromagnetic inspection of pipes or tubular constructions other than wellbore casings. In one example, the apparatus may be configured for electromagnetic inspection of a radially outer surface of a generally tubular structure.

Another aspect disclosed by the above-referenced described example embodiments includes a method comprising:

moving an inspection tool lengthwise along a wellbore, the inspection tool having a plurality of azimuthally spaced rolling probe devices;

during movement of the inspection tool along the wellbore, rolling the plurality of rolling probe devices along a cylindrical inner surface of a casing that lines the wellbore, each rolling probe device being in rolling contact engagement with the casing at a respective azimuthal position; and at each of the plurality of rolling probe devices, during rolling contact engagement with the casing, capturing electromagnetic measurement data by use of measuring instrumentation carried by the respective rolling probe device, the electromagnetic measurement data being indicative of one or more structural properties of the casing.

The capturing of the electromagnetic measurement data may comprise:

transmitting an excitation signal via one or more electromagnetic transmitters forming part of the measurement instrumentation; and measuring, at one or more electromagnetic receivers forming part of the measurement instrumentation, a received signal substantially caused by transmission of the excitation signal.

The electronic measurement data may comprise a transfer function, the method further comprising producing the transfer function in a signal processing operation comprising normalization of the received signal based at least in part on the excitation signal. The one or more electromagnetic transmitters may be selected from the group comprising: inductive transmitters, capacitive transmitters, and galvanic transmitters. The one or more electromagnetic receivers may be selected from the group comprising: inductive receivers, capacitive receivers, and galvanic receivers.

The method may further comprise processing the electromagnetic measurement data to identify one or more structural defects of the casing, the processing comprising:

deriving from the electromagnetic measurement data casing property information that indicates location-variable values for one or more electromagnetic properties of the casing;

based at least in part on the casing property information, identifying one or more areas of the casing in which the one or more electromagnetic properties of the casing fall outside a predefined target range; and indicating each of the one or more identified areas as a corroded area of the casing.

The one or more electromagnetic properties may be selected from the group comprising: conductivity, and permeability.

The casing may comprise a longitudinal extending series of co-axial casing sections that are connected together end-to-end, with the method further comprising:

establishing different respective baseline measurements for the one or more electromagnetic properties of different casing sections, such that, for at least some of the casing sections, different casing sections have different baseline measurements for a particular electromagnetic property, and wherein the identifying of the one or more areas of the casing is based at least in part on the different respective baseline measurements, the electromagnetic properties of different casing sections being assessed based at least in part on different correspond baseline measurements.

The method may further comprise:

processing the electromagnetic measurement data captured by the plurality of rolling probe devices; and based on the processing, generating a casing image representing structural features of the casing, with image information for different azimuthal positions of the casing image being based on electromagnetic measurement data captured by respectively corresponding ones of the plurality of rolling probe devices.

The plurality of rolling probe devices may be arranged such that a cumulative azimuthal coverage of the plurality of rolling probe devices covers an entire azimuthal extent of the interior cylindrical surface of the casing.

The method may further comprise:

generating multiple casing images based on multiple respective rolling probe data sets captured at different times, to produce a set of time-staggered casing images; and based on the set of time-staggered casing images, generating an animated casing image that provides a graphic representation of changes to the structural features of the casing over a particular time interval.

The method may further comprise, in an automated operation using one or more computer processors, performing image processing on the casing image, to identify one or more structural defects of the casing.

Modules, Components, and Logic

Certain embodiments are described herein as including logic or a number of components, modules, or mechanisms. Modules may constitute either software modules, with code embodied on a non-transitory machine-readable medium (i.e., such as any conventional storage device, such as volatile or non-volatile memory, disk drives or solid state storage devices (SSDs), etc.), or hardware-implemented modules. A hardware-implemented module is a tangible unit capable of performing certain operations and may be configured or arranged in a certain manner. In example embodiments, one or more computer systems (e.g., a standalone, client, or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry or in temporarily configured circuitry (e.g., configured by software), may be driven by cost and time considerations.

Accordingly, the term "hardware-implemented module" should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., Application Program Interfaces (APIs).)

Figure 12:
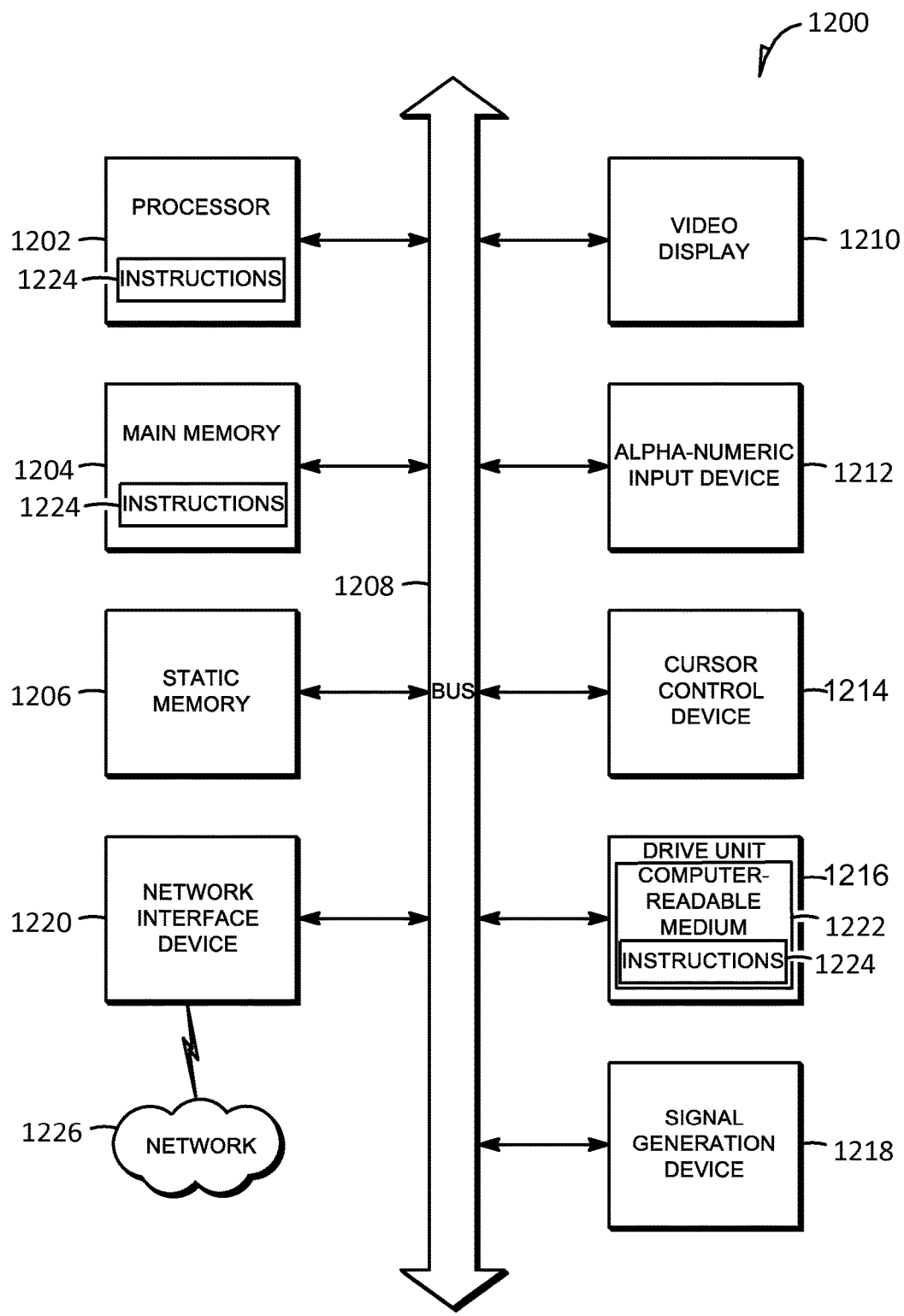
FIG. 12 is a diagrammatic representation of machine in the example form of a computer system within which a set of instructions for causing the machine to perform a method for estimating subsurface formation and invasion properties may be executed.

FIG. 12 shows a diagrammatic representation of a machine in the example form of a computer system 1200 within which a set of instructions 1224 may be executed for causing the machine to perform any one or more of the methodologies discussed herein. For example, the surface computer system 366 (FIG. 3) or any one or more of its components may be provided by the system 1200.

In alternative embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1200 includes a processor 1202 (e.g., a central processing unit (CPU) a graphics processing unit (GPU) or both), a main memory 1204 and a static memory 1206, which communicate with each other via a bus 1208. The computer system 1200 may further include a video display unit 1210 (e.g., a liquid crystal display (LCD) or a cathode ray tube (CRT)). The computer system 1200 also includes an alpha-numeric input device 1212 (e.g., a keyboard), a cursor control device 1214 (e.g., a mouse), a disk drive unit 1216, a signal generation device 1218 (e.g., a microphone/speaker) and a network interface device 1220.

The disk drive unit 1216 includes a machine-readable or computer-readable storage medium 1222 on which is stored one or more sets of instructions 1224 (e.g., software) embodying any one or more of the methodologies or functions described herein. The instructions 1224 may also reside, completely or at least partially, within the main memory 1204 and/or within the processor 1202 during execution thereof by the computer system 1200, the main memory 1204 and the processor 1202 also constituting non-transitory machine-readable media. The instructions 1224 may further be transmitted or received over a network 1226 via the network interface device 1220.

While the machine-readable storage medium 1222 is shown in an example embodiment to be a single medium, the term "machine-readable medium" should be taken to include a single medium or multiple media (e.g., a centralized or distributed database and/or associated caches and servers) that store the one or more sets of instructions 1224. The term "machine-readable medium" shall also be taken to include any medium that is capable of storing a set of instructions for execution by the machine and that cause the machine to perform any one or more of the methodologies of this disclosure. The term "machine-readable medium" shall accordingly be taken to include, but not be limited to, solid-state memory devices of all types, as well as optical and magnetic media.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus for nondestructive structural inspection within a wellbore, the apparatus comprising:
a tool body configured to be placed in a wellbore; and
one or more rolling probe assemblies mounted on the tool body and configured to measure one or more properties of a target structure, each rolling probe assembly comprising:
a roller configured to revolve relative to the tool body and having a tread surface that bears against the target structure to allow rolling contact engagement of the tread surface with the target structure; and
measuring instrumentation within the roller, the measuring instrumentation extending along the tread surface at or adjacent an exterior of the roller, the measuring instrumentation configured for capturing electromagnetic measurement data during rolling contact engagement of the tread surface with the target structure, the electromagnetic measurement data being indicative of the one or more properties of the target structure.

2. The apparatus of claim 1, wherein each roller is rotatably mounted on the tool body about a respective axis of rotation, the tread surface being defined by a radially outer surface of the roller.

3. The apparatus of claim 1, wherein each roller is of a resiliently compressible material, and wherein each rolling probe assembly further comprises an urging mechanism for urging the corresponding roller into contact with the target structure such that a contact interface between the roller and the target structure comprises a substantially nonlinear area.

4. The apparatus of claim 1, wherein each roller comprises a roller body that defines a circumferentially extending substrate surface, the measurement instrumentation comprising printed electronic circuitry carried on the substrate surface.

5. The apparatus of claim 4, wherein the measuring instrumentation comprises a flexible printed circuit board mounted on the substrate surface.

6. The apparatus of claim 1, wherein the measuring instrumentation comprises a substantially uninterrupted, regularly spaced series of sensor antennae, the series extending circumferentially along the tread surface of the roller.

7. The apparatus of claim 1, wherein each roller comprises:
a carrier body that defines a substrate surface on which the measurement instrumentation is carried; and
a barrier layer that covers the substrate surface and the measurement instrumentation such that the tread surface of the roller is defined by an outer surface of the barrier layer, the measurement instrumentation being located beneath the tread surface.

8. The apparatus of claim 1, wherein each roller comprises a flexible web, each rolling probe assembly further comprising a guide arrangement having two or more guide wheels rotatable about parallel, spaced rotational axes, the web being mounted on the guide arrangement for guided revolving movement about the two or more guide wheels in an endless loop.

9. The apparatus of claim 1, wherein the apparatus is configured to measure the one or more properties of the target structure by rolling contact engagement with an interior cylindrical surface of the target structure, the tool body being configured for movement along a longitudinal axis of the interior cylindrical surface, and the one or more rolling probe assemblies comprising a plurality of rolling probe assemblies that are circumferentially spaced about the tool body for simultaneous rolling contact engagement with the interior cylindrical surface at different circumferential positions.

10. The apparatus of claim 9, wherein the tool body is elongate, to extend lengthwise along the longitudinal axis of the interior cylindrical surface, and wherein the plurality of rolling probe assemblies are arranged in two or more axially spaced sets of rolling probe assemblies, each set of rolling probe assemblies comprising two or more circumferentially spaced, axially aligned rolling probe assemblies.

11. The apparatus of claim 10, wherein the two or more sets of rolling probe assemblies are substantially identical in spatial arrangement, but are angularly displaced relative to each other, so that the rollers of the rolling probe assemblies of respective sets are axially misaligned.

12. The apparatus of claim 11, wherein the plurality of rolling probe assemblies cumulatively provide full circumferential coverage of the interior cylindrical surface of the target structure.

13. The apparatus of claim 9, wherein each rolling probe assembly comprises an undercarriage that mounts the associated roller on the tool body such that a radial spacing between the tool body and the roller, relative to the longitudinal axis, is dynamically variable.

14. The apparatus of claim 10, wherein each rolling probe assembly comprises an urging mechanism configured to urge the associated roller radially outwards and into contact with the interior cylindrical surface.

15. The apparatus of claim 9, wherein the apparatus is configured for electromagnetic inspection of a wellbore casing, the tool body being configured for insertion in and lengthwise movement along the wellbore casing.

16. A method comprising:
moving an inspection tool lengthwise along a wellbore, the inspection tool having a tool body and a plurality of azimuthally spaced rolling probe assemblies, wherein each rolling probe assembly includes,
a roller configured to revolve relative to the tool body and having a tread surface that bears against a target structure to allow rolling contact engagement of the tread surface with the target structure; and
measuring instrumentation within the roller, the measuring instrumentation extending along the tread surface at or adjacent an exterior of the roller, the measuring instrumentation configured for capturing electromagnetic measurement data during rolling contact engagement of the tread surface with the target structure, the electromagnetic measurement data being indicative of one or more properties of the target structure;
during movement of the inspection tool along the wellbore, rolling the plurality of rolling probe assemblies along a cylindrical inner surface of a casing having a casing linage that lines the wellbore, each rolling probe assembly being in rolling contact engagement with the casing linage at a respective azimuthal position; and
at each of the plurality of rolling probe assemblies, during rolling contact engagement with the casing linage, capturing electromagnetic measurement data by use of measuring instrumentation carried by the respective rolling probe assembly, the electromagnetic measurement data being indicative of one or more structural properties of the casing.

17. The method of claim 16, further comprising:
processing the electromagnetic measurement data captured by the plurality of rolling probe assemblies; and based on the processing, generating a casing image representing structural features of the casing, with image information for different azimuthal positions of the casing linage being based on electromagnetic measurement data captured by respectively corresponding ones of the plurality of rolling probe assemblies.

18. The method of claim 17, wherein the plurality of rolling probe assemblies are arranged such that a cumulative azimuthal coverage of the plurality of rolling probe assemblies covers an entire azimuthal extent of an interior cylindrical surface of the casing.

19. The method of claim 17, further comprising:
generating multiple casing linages based on multiple respective rolling probe data sets captured at different times, to produce a set of time-staggered casing images; and
based on the set of time-staggered casing images, generating an animated casing image that provides a graphic representation of changes to the structural features of the casing over a particular time interval.

20. The method of claim 17, further comprising, in an automated operation using one or more computer processors, performing image processing on the casing image, to identify one or more structural defects of the casing.

* * * * *